(12) United States Patent
Huang et al.

(10) Patent No.: US 6,887,362 B2
(45) Date of Patent: *May 3, 2005

(54) DIELECTROPHORETIC SEPARATION AND IMMUNOASSAY METHODS ON ACTIVE ELECTRONIC MATRIX DEVICES

(75) Inventors: Ying Huang, San Diego, CA (US); Karla Ewalt, San Diego, CA (US); Robert Haigis, San Diego, CA (US); Anita Forster, Santee, CA (US); Michael K. Krihak, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 435 days.

This patent is subject to a terminal disclaimer.

(21) Appl. No.: 10/072,660

(22) Filed: Feb. 6, 2002

(65) Prior Publication Data

US 2003/0146100 A1 Aug. 7, 2003

(51) Int. Cl.$^7$ ............................................. G01N 27/26
(52) U.S. Cl. ................. 204/547; 204/643; 435/173.7; 435/173.9; 435/6; 435/7.2; 435/7.1; 435/285.2; 435/287.2; 435/306.1; 422/68.1; 422/50
(58) Field of Search ................................ 204/547, 643; 435/173.7, 173.9, 6, 7.2, 7.1, 285.2, 287.2, 306.1; 422/68.1, 50

(56) References Cited

U.S. PATENT DOCUMENTS 3,346,479 A 10/1967 Natelson (Continued)

FOREIGN PATENT DOCUMENTS

| DE | 2051715 A | 4/1972 |
|----|-----------|--------|
| EP | 0047645 B1 | 11/1984 |
| EP | 0243501 A1 | 11/1987 |
| GB | 1359944 A | 7/1974 |
| GB | 2118975 A | 11/1983 |
| JP | 55-152027 A | 11/1980 |
| JP | 56-167419 A | 12/1981 |
| JP | 59-215838 A | 12/1984 |
| JP | 59-227131 A | 12/1984 |
| JP | 01163049 A | 6/1989 |
| JP | 02292013 A | 12/1990 |
| SU | 434985 A1 | 1/1975 |
| SU | 616568 A1 | 7/1978 |
| WO | WO 01/13126 A1 | 2/2001 |

OTHER PUBLICATIONS

Yang et al, "An integrated stacked microlaboratory for biological agent detection with DNA and immunoassays," Biosensors and Bioelectronics, vol. 17, pp. 605–618, (2002).*

(Continued)

*Primary Examiner*—Alan Diamond
(74) *Attorney, Agent, or Firm*—O'Melveny & Myers LLP

(57) ABSTRACT

This invention relates to devices and methods for performing active, multi-step molecular and biological sample preparation and diagnostic analyses employing immunochemical techniques. It relates generally to bioparticle separation, bioparticle enrichment, and electric field-mediated immunochemical detection on active electronic matrix devices utilizing AC and DC electric fields. More specifically, the invention relates to devices and methods for sample preparation/manipulation, immunoimmobilization, and immunoassays, all of which can be conducted on one or more active electronic chip devices within a single system. These manipulations are useful in a variety of applications, including, for example, detection of pathogenic bacteria and biological warfare agents, point-of-care diagnostics, food or medical product quality control assays, and other biological assays.

14 Claims, 14 Drawing Sheets

U.S. PATENT DOCUMENTS

| | | | |
|---|---|---|---|
| 3,375,187 A | 3/1968 | Buchler | |
| 3,533,933 A | 10/1970 | Strauch | |
| 3,539,493 A | 11/1970 | Dorman | |
| 3,616,454 A | 10/1971 | Levy et al. | |
| 3,627,137 A | 12/1971 | Bier | |
| 3,640,813 A | 2/1972 | Nerenberg | |
| 3,697,405 A | 10/1972 | Butter et al. | |
| 3,773,648 A | 11/1973 | Van Welzen et al. | |
| 3,791,950 A | 2/1974 | Allington | |
| 3,902,986 A | 9/1975 | Nees | |
| 3,980,546 A | 9/1976 | Caccavo | |
| 4,111,785 A | 9/1978 | Roskam | |
| 4,326,934 A | 4/1982 | Pohl | |
| 4,390,403 A | 6/1983 | Batchelder | |
| 4,441,972 A | 4/1984 | Pohl | |
| 4,479,861 A | 10/1984 | Hediger | |
| 4,617,102 A | 10/1986 | Tomblin et al. | |
| 4,661,451 A | 4/1987 | Hansen | |
| 4,699,706 A | 10/1987 | Burd et al. | |
| 4,737,259 A | 4/1988 | Ogawa et al. | |
| 4,740,283 A | 4/1988 | Laas et al. | |
| 4,787,963 A | 11/1988 | MacConnell | |
| 4,877,510 A | 10/1989 | Chen | |
| 4,881,107 A | 11/1989 | Matsushita | |
| 4,908,112 A | 3/1990 | Pace | |
| 4,936,963 A | 6/1990 | Mandecki et al. | |
| 4,971,670 A | 11/1990 | Faupel et al. | |
| 5,062,942 A | 11/1991 | Kambara et al. | |
| 5,078,853 A | 1/1992 | Manning et al. | |
| 5,085,756 A | 2/1992 | Swedberg | |
| 5,126,022 A | 6/1992 | Soane et al. | |
| 5,139,637 A | 8/1992 | MacConnell | |
| 5,151,189 A | 9/1992 | Hu et al. | |
| 5,151,165 A | 11/1992 | Huynh | |
| 5,202,010 A | 4/1993 | Guzman | |
| 5,209,831 A | 5/1993 | MacConnell | |
| 5,217,593 A | 6/1993 | MacConnell | |
| 5,269,931 A | 12/1993 | Hu et al. | |
| 5,296,114 A | 3/1994 | Manz | |
| 5,340,449 A | 8/1994 | Shukla | |
| 5,344,535 A | 9/1994 | Betts et al. | |
| 5,376,249 A | 12/1994 | Afeyan et al. | |
| 5,382,511 A | 1/1995 | Stapleton | |
| 5,427,664 A | 6/1995 | Stoev et al. | |
| 5,434,049 A | 7/1995 | Okano | |
| 5,445,934 A | 8/1995 | Fodor et al. | |
| 5,451,500 A | 9/1995 | Stapleton | |
| 5,527,670 A | 6/1996 | Stanley | |
| 5,569,367 A | 10/1996 | Betts et al. | |
| 5,589,047 A | 12/1996 | Coster et al. | |
| 5,593,580 A | 1/1997 | Kopf | |
| 5,605,662 A | 2/1997 | Heller et al. | |
| 5,632,957 A | 5/1997 | Heller et al. | |
| 5,653,859 A | 8/1997 | Parton et al. | |
| 5,653,939 A | 8/1997 | Hollis et al. | |
| 5,728,267 A | 3/1998 | Flaherty | |
| 5,795,457 A | 8/1998 | Pethig et al. | |
| 5,814,200 A | 9/1998 | Pethig et al. | |
| 5,849,486 A | 12/1998 | Heller et al. | |
| 5,858,192 A | 1/1999 | Becker et al. | |
| 6,017,696 A | 1/2000 | Heller | |
| 6,048,690 A | 4/2000 | Heller et al. | |
| 6,051,380 A * | 4/2000 | Sosnowski et al. | 435/6 |
| 6,054,270 A | 4/2000 | Southern | |
| 6,071,394 A * | 6/2000 | Cheng et al. | 204/547 |
| 6,099,803 A | 8/2000 | Ackley et al. | |
| 6,113,768 A | 9/2000 | Fuhr et al. | |
| 6,245,508 B1 * | 6/2001 | Heller et al. | 435/6 |
| 6,254,827 B1 * | 7/2001 | Ackley et al. | 422/68.1 |
| 6,280,590 B1 * | 8/2001 | Cheng et al. | 204/463 |
| 6,309,601 B1 | 10/2001 | Juncosa et al. | |
| 6,335,161 B1 | 1/2002 | Martin et al. | |
| 6,518,022 B1 * | 2/2003 | Sosnowski et al. | 435/6 |
| 6,726,880 B1 * | 4/2004 | Ackley et al. | 422/68.1 |
| 2001/0045359 A1 * | 11/2001 | Cheng et al. | 204/547 |
| 2003/0146145 A1 * | 8/2003 | Krotz et al. | 210/243 |
| 2004/0011650 A1 * | 1/2004 | Zenhausern et al. | 204/547 |

OTHER PUBLICATIONS

Cheng, J., et al. "Preparation and Hybridization Analysis of DNA/RNA From E.coli On Microfabricated Bioelectronic Chips", Nature/Biotechnology, 16, pp. 541–546 (1998).

Gilles, P.N., et al. "Single Nucleotide Polymorphic Discrimination By An Electronic Dot Blot Assay On Semiconductor Chips", Nature/Biotechnology v. 17, #4, pp. 365–370 (1999).

Heller, M.J. "An Active Microelectronics Device For Multiplex Analysis", IEEE Engineering in Medicine and Biology, pp. 100–104 (Mar./Apr. 1996).

Huang, Y., et al. "Electric Manipulation of Bioparticles and Macromolecules on Microfabricated Electrodes" Analytical Chemistry, v.73, n.7, pp. 1549–1559 (2001).

Manz, A., et al., "Miniaturized Total Chemical Analysis System: A Novel Concept for Chemical Sensing" Sensors and Actuators B1, pp. 244–248 (1990).

Becker et al., "The removal of human leukemia cells from blood using interdigitated microelectrodes," J. Phys. D: Appl. Phys. 27 (1994) 2659–2662.

Camag, Inc. Product Literature, date unknown.

Edman, C.F. et al., "Electric field directed nucleic acid hybridization on microchips", Nucleic Acids Research, vol. 25, No. 24, pp. 4907–4914, (1997).

Fuhr et al., Positioning and Manipulation of Cells and Microparticles Using Miniaturized Electric Field Traps and Travelling Waves; Sensors and Materials, vol. 7, No. 2 (1995) 131–146.

Fuhr, G., "Cell Manipulation and Cultivation Under AC Electric Field Influence in Highly Conductive Culture Media", Biochem. Biophys. Acta, vol. 1158, pp. 40–46, (1993).

Markx et al., "Dielectrophoretic characterization and separation of micro–organisms", Microbiology (1994) 140, 585–591.

Markx et al., "Dielectrophoretic separation of bacteria using a conductivity gradient," Journal of Biotechnology, 51 (1996) 175–180.

Pethig R. et al., "Positive and negative dielectrophoretic collection of colloidal particles using interdigitated castellated mocroelectrodes," J. Phys. D: Appl. Phys, 24 (1992) 881–888.

Pethig, R., "Dielectrophoresis: Using Inhomogeneous AC Electrical Fields to Separate and Manipulate Cells," Critical Reviews in Biotechnology, 16(4):331–348 (1996).

Scanning Laser Microscopy Lab, Web Site print–out, http://www.science.uwaterloo.ca/research_groups/confocal (1997).

Sosnowski, R. et al., "Rapid determination of single base mismatch mutations in DNA hybrids by direct electric field control", Proc. Natl. Acad. Sci. USA, vol. 94, pp. 1119–1123, Feb. 1997.

Tony Wilson and Colin Sheppard, "Theory and Practice of Scanning Optical Microscopy", Academic Press, 1984 (ISBN–0–12–757760–2).

Wang et al., "Dielectrophoretic Manipulation of Particles," IEEE Transactions on Industry Applications, vol. 33, No. 3 (May/Jun. 1997).

Wang, X., "A Unified Theory of Dielectrophoresis and Travelling Wave Dielectrophoresis", J. Phys. D: Appl. Phys., vol. 27, pp. 1571–1574, 1994.

Washizu, M., "Molecular Dlelectrophoresis of Biopolymers", IEEE Trans. Industry Applicat., vol. 30, pp. 835–843, 1994.

* cited by examiner

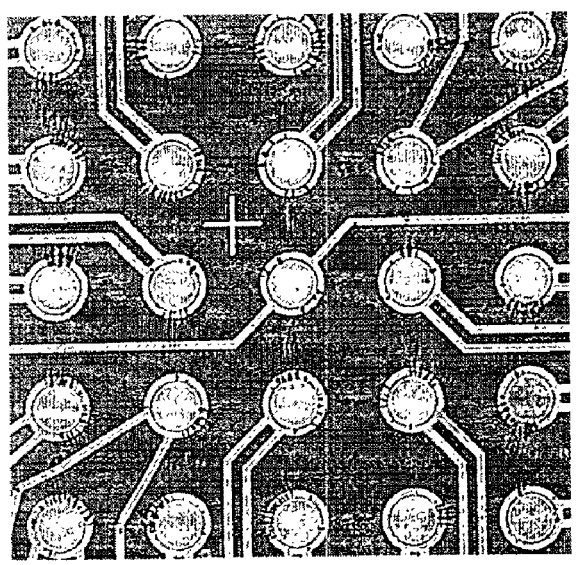
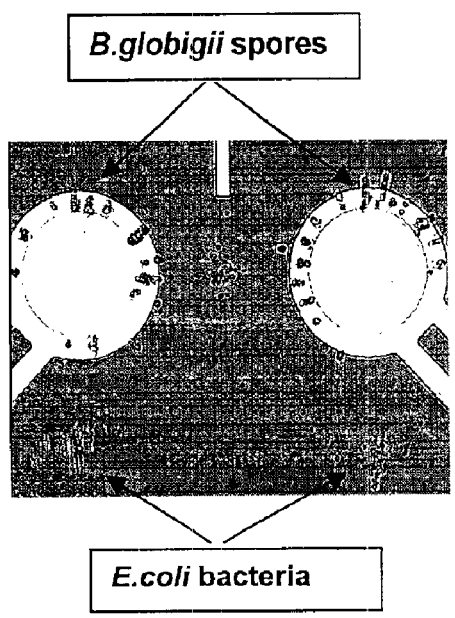
Figure 9A                    Figure 9B

US 6,887,362 B2

DIELECTROPHORETIC SEPARATION AND IMMUNOASSAY METHODS ON ACTIVE ELECTRONIC MATRIX DEVICES

FIELD OF THE INVENTION

This invention relates to devices and methods for performing active, multi-step molecular and biological sample preparation and diagnostic analyses employing immunochemical techniques. It relates generally to bioparticle separation, bioparticle enrichment, and electric field-mediated immunochemical detection on active electronic matrix devices utilizing AC and DC electric fields. More specifically, the invention relates to devices and methods for sample preparation/manipulation, immunoimmobilization, and immunoassays, all of which can be conducted on one or more active electronic chip devices within a single system. These manipulations are useful in a variety of applications, including, for example, detection of pathogenic bacteria and biological warfare agents, point-of-care diagnostics, food or medical product quality control assays, and other biological assays.

BACKGROUND OF THE INVENTION

The basis for many molecular-biological and immunoassays, diagnostic assays and tests, among other things, include the steps of obtaining a sample suspected of containing cellular material of interest (e.g., blood, tissue, food or water samples, etc), separating out the cellular material of interest, disrupting or lysing the cells of interest to release the crude lysate (containing proteins, nucleic acids, cellular components, etc.), purifying the crude lysate (i.e. removing unwanted cellular debris), and performing some analysis on the lysate to detect the molecules or components of interest.

The current methods commonly used in biological laboratories for manipulation, concentration, and separation of bioparticles and macromolecules include optical tweezers, fluorescence or magnetic field activated cell sorting, centrifugation, filtration, and electric field-based manipulations and separations. Among these methods, the electric field based approach is well suited for miniaturization because of the relative ease of microscale generation and structuring of an electric field on microchips.

Depending on the nature of bioparticles to be manipulated, different types of electric fields can be applied: (1) a DC field for electrophoresis (EP) of charged bioparticles; (2) a nonuniform AC field for dielectrophoresis (DEP) of polarized bioparticles; (3) the combined AC and DC fields for manipulating charged and neutral bioparticles. Because most biological cells have similar electrophoretic mobilities, EP for manipulation of cells has limited applications. On the other hand, DEP has been successfully applied on microchip scales to manipulate and separate a variety of biological cells including bacteria, yeast, and mammalian cells.

Large-scale dielectrophoresis has become a popular technique for separating microparticles which are either charged or uncharged in solution. These techniques are usually performed in a glass slide based device having exposed (i.e. naked) interdigitated electrodes plated on the surface of the slide and having a flow chamber with a volume of several hundred microliters. Cells are separated in such devices based on their dielectric properties by choosing separation buffer(s) with appropriate conductivity and an AC signal with a suitable amplitude and frequency. These prior devices have several problems, including the following. A first problem is that both separated and unseparated cells bind nonspecifically to the exposed glass surface of the slide and to the exposed electrode surfaces. A second problem is that the volume of the flow chamber (several hundred $\mu$l) is so large that thermal convection disturbs and pushes off cells initially retained by the electrodes. A third problem is that washing off any undesired cells is not easily accomplished without disturbing the cells that are desirably retained on the electrodes, as the desired cells and electrodes stand in the way of fluidic flow and, hence, block the wash flow containing any undesired cells.

To separate intracellular organelles and molecular components, cells must be disrupted. Disrupting or lysing cells releases the crude DNA and RNA material along with other cellular constituents. Well known electronic cell electroporation lysing techniques are conventionally performed by applying a series of high voltage DC pulses in a macrodevice, as opposed to a microchip-based device. These conventional electronic lysis/electroporation techniques have several problems. A first problem is that the electronic lysis conditions specified by commercial macrodevices do not release medium to large proteins, organelles, and DNA molecules of high molecular weight (larger than 20 Kb) because they do not fit through the pores created in the cell membrane by the prior lysing methods. A second problem is that some molecules of interest originally released in the lysis chamber are lost due to their non-specific binding to the surface of the lysis chamber. A third problem is that the conventional electronic lysis macrodevice works as a stand-alone unit such that both dielectrophoretic cell separation and electronic lysis cannot be performed on the same module.

The crude lysate is then purified (i.e., undesired cellular debris is washed off or separated), and then the purified lysate is subjected to various enzymatic reaction(s) and/or other processing steps to prepare the lysate for detection and analysis. These conventional preparation and processing techniques have several problems, including the following. A first problem is that the steps of sample preparation and processing are typically performed separately and apart from the other main steps of the analysis. In addition, most of these techniques involve carrying out numerous operations (e.g., pipetting, centrifugations, and electrophoresis) on a large number of samples. They are often complex and time consuming, and generally require a high degree of skill. Many a technique is limited in its application by a lack of sensitivity, specificity, or reproducibility.

Attempts have been made to use dielectrophoresis to separate and identify cells. For example, U.S. Pat. No. 4,326,934 to Herbert discloses a method and apparatus for cell classification by continuous dielectrophoresis. Cells were separated by making use of both the positive and negative dielectrophoretic movement of cell particles. Separated cells were allowed to be characterized and/or classified by viewing the characteristic deflection distance of cells moving through the two electrodes.

Also, U.S. Pat. No. 5,344,535 to Walter et al. discloses a method and apparatus for the characterization of microorganisms and other particles by dielectrophoresis. Cells were characterized by matching their signature dielectrophoretic collection rates. U.S. Pat. No. 5,569,367 to Walter et al. discloses a method and apparatus for separating a mixture using a pair of interdigitated electrodes. The apparatus used two energized interdigitated electrodes that obstruct straight through flow of cells and further separate different types of cells into fractions by applying a non-uniform alternating field. The electrode structure is comprised of interleaved grid-like structures aligned to obstruct flow through the structure.

In addition, attempts have been made to combine certain processing steps or substeps together. For example, various attempts have been made to describe integrated systems formed on a single chip or substrate, wherein multiple steps of an overall sample preparation and diagnostic system would be included. For example, A. Manz et al., in "Miniaturized Total Chemical Analysis System: A Novel Concept For Chemical Sensing", *Sensors And Actuators*, B1 (1990), pp. 244–248, describe a 'total chemical analysis system' (TAS) which comprises a modular construction of a miniaturized TAS. Sampling, sample transport, any necessary chemical reactions, chromatographic separations as well as detection were to be automatically carried out.

Traditional immunoassay methods utilizing microtiterplate formats, dipsticks, etc., are labor and time extensive. Multiple steps requiring human intervention either during the process or between processes are sub-optimal in that there is a possibility of contamination and operator error. Further, the use of multiple machines or complicated robotic systems for performing the individual processes is often prohibitive except for the largest laboratories, both in terms of the expense and physical space requirements.

As is apparent from the preceding discussion, various methods exist to provide traditional means of immunoassay analysis. However, for the reasons stated above, these traditional techniques involve the disadvantages of multiple sample/analyte transfer steps, and often require large sample volumes to obtain the desired sensitivity and specificity for the assay.

SUMMARY OF THE INVENTION

The present invention represents a substantial improvement in previous active electronic matrix chip constructs and dielectrophoretic methods by utilizing immunochemical components to perform specific capture and/or reporting functions in methods combining dielectrophoresis (DEP) and electrophoresis (EP). By utilizing active electronic matrix chip devices, the speed of traditional immunochemical labeling and capture functions can be dramatically increased, while reducing the amount of non-specific background binding. When combined with DEP methods on the active electronic matrix chip devices, sample preparation and immunochemical analysis can be done quickly and efficiently in the same instrument volume.

Several benefits may be gained from approach. First, EP is well suited for manipulating charged macromolecules whereas DEP is particularly suited for manipulating large sized bioparticles (micron or greater). The combined use exploits the advantages of both EP and DEP, and provides an effective approach for detecting and assaying bioparticles. Second, EP and DEP can be performed with the same set of electrodes under different signal excitations. Such a method is particularly applicable to bioelectronic chips, where the individually addressable electrode array allows flexible and versatile application of EP and DEP in many different bioanalytical processes including cell enrichment and separation, target concentration, and electric field-driven DNA hybridization and immunoassays. Finally, because different bioparticles (e.g. bacteria versus spores) can have different dielectric properties, and as a consequence respond to an applied AC field differentially, direct incorporation of DEP for selectively manipulating target bioparticles in a bioassay provides additional specificity to the assay.

Thus, this invention broadly relates to active electronic matrix devices and methods for performing immunoreagent capture and/or detection assays using dielectrophoresis to perform cell sorting and isolation of bioparticles. Immunoreagent components may be utilized during DEP separation and isolation of bioparticles to enhance specific retention and localization of the bioparticles, and may also be used to detect the isolated bioparticles by EP mediated detection immunoreactions. Further, electronic cell lysis may be utilized to extract target proteins, and other sub-cellular constituents, from isolated cell bioparticles of interest. After cell lysis, charged sub-cellular constituents of interest may be transported eletrophoretically to microlocations of the active electronic matrix devices for electric field-mediated immunodetection on the devices.

A first aspect of this invention provides methods for isolating and immobilizing at least one bioparticle of interest on an active electronic matrix chip device. The basic device comprises: a substrate, individually addressable electrodes on the substrate, and a permeation layer overlying a plurality of the electrodes on the substrate, wherein portions of the permeation layer over the electrodes form microlocations of the active electronic matrix chip device, and wherein at least one capture immunoreagent specific for the bioparticle of interest is attached to the permeation layer of the device at or between a plurality of microlocations. In general, the methods of this aspect of the invention comprise:

a) Introducing onto the active electronic matrix device a sample solution containing the bioparticle of interest, wherein the sample solution is of a conductivity suitable for dielectrophoretic isolation of the bioparticle of interest. As discussed herein, the suitable conductivity of the solution may be determined by theoretical calculation or by standard empirical tests, depending on the known characteristics of the bioparticle.

b) Passing an alternating current through selected electrodes on the active electronic matrix chip device, wherein the electrodes are selected to produce areas of high alternating current field strength and low alternating current field strength at predetermined positions on the active electronic matrix chip device (e.g., in checkerboard, square wall, concentric square, or other patterns), wherein the alternating current is supplied at a suitable voltage and frequency for dielectrophoretic isolation of the bioparticle of interest, and further wherein the capture immunoreagent specific for the bioparticle of interest are located at one or more predetermined positions of alternating current field strength at which the bioparticle of interest is predicted to aggregate (e.g., at or between microlocations of the device); and c) Maintaining the alternating current in (b) for a sufficient length of time to allow the capture immunoreagent to bind to the bioparticle of interest, thereby immobilizing the bioparticle.

A second aspect of the invention provides methods for isolating and detectably labeling at least one bioparticle of interest on an active electronic matrix chip device. The basic device is described above, except that the presence of capture immunoreagents is optional. Such reagents are attached at microlocations of the device, when present. The methods generally comprise:

a) An introducing step as described above;

b) Passing an alternating current through selected electrodes on the active electronic matrix chip device, wherein the electrodes are selected to produce areas of high alternating current field strength and low alternating current field strength at predetermined positions on the active electronic matrix chip device (e.g., using the above described patterns), wherein the alternating current is supplied at a suitable voltage and frequency for dielectrophoretic isolation of the bioparticle of interest, and further wherein one or more predetermined positions of alternating current field strength at which the bioparticle of interest is predicted to aggregate are at one or more "aggregate" microlocations of the active electronic matrix chip device;

c) Maintaining the alternating current in (b) for a sufficient length of time to allow the bioparticle of interest to aggregate at the aggregate microlocations;

d) Introducing onto the active electronic matrix chip device a solution comprising a detection immunoreagent specific for the bioparticle of interest;

e) Passing a direct current through one or more aggregate microlocations, wherein the electrodes under the aggregate microlocations are biased so as to attract the detection immunoreagent to the aggregate microlocations from the solution (e.g., a positive bias under the solution conditions generally described in the examples); and f) Maintaining the direct current in (e) for a sufficient time to allow the detection immunoreagent to bind to the bioparticle of interest at the aggregate microlocation, thereby detectably labeling the bioparticle.

In some embodiments of this aspect, the bioparticles of interest may be further immobilized at the aggregate microlocations as described in the first aspect. In other embodiments, the bioparticles may adhere to the permeation layer at the aggregate microlocations due to the characteristics (chemical, physical, etc.) of the bioparticles.

A third aspect of the invention provides methods for isolating and immobilizing at least one sub-cellular constituent of a cellular bioparticle of interest in a system comprising one or more fluidly connected active electronic matrix chip devices. Thus, in some embodiments of this aspect, the system may comprise one active electronic matrix chip which is used for DEP isolation, lysing, and EP immunoassay functions. In other embodiments, the system may comprise separate active electronic matrix chip devices for the DEP and lysing functions, and another active electronic matrix chip device for the EP immunoassay functions. The basic devices are as described in the second aspect of the invention. The methods of the third aspect generally comprise:

a) An introduction step as described above;

b) Passing an alternating current through selected electrodes on an active electronic matrix chip device in the system, wherein the electrodes are selected to produce areas of high alternating current field strength and low alternating current field strength at predetermined positions on the active electronic matrix chip device (e.g., using the patterns described above), wherein the alternating current is supplied at a suitable voltage and frequency for dielectrophoretic isolation of the cellular bioparticle of interest;

c) Maintaining the alternating current in (b) for a sufficient length of time to allow the cellular bioparticle of interest to aggregate at the predetermined positions;

d) Electronically lysing the aggregated cellular bioparticle of interest to release one or more sub-cellular constituents of interest (e.g., proteins, proteoglycans, glycoproteins, glycosides, supramolecular complexes, and organelles or organelle fragments) from the cellular bioparticle;

e) passing a direct current through one or more "capture" microlocations on one of the devices in the system, wherein the electrodes under the capture microlocations are biased so as to attract at least one sub-cellular constituent of interest to the capture microlocations, and wherein at least one capture immunoreagent specific for the sub-cellular constituent of interest is attached at the capture microlocations; and f) Maintaining the direct current in (e) for a sufficient time to allow the capture immunoreagent to bind to the sub-cellular constituent of interest at the capture microlocation, thereby immobilizing the sub-cellular constituent.

In some embodiments of this aspect, the bioparticles of interest may be further immobilized at the aggregate microlocations as described in the first aspect. In other embodiments, the bioparticles may adhere to the permeation layer at the aggregate microlocations due to the characteristics (chemical, physical, etc.) of the bioparticles. In other embodiments, the bioparticles may simply be held in place by the AC field until they are lysed.

In the above aspects of the invention, optional washing steps may be included to remove unwanted sample components or cellular constituents, or excess detection immunoreagents, at appropriate points in the methods. Additional labeling and detection steps may also be incorporated into the first and third aspects in order to qualify and/or quantify the isolation of bioparticles at particular sites on the device, or binding of the bioparticles or cell constituents of interest to the capture immunoreagents.

Other aspects of the present invention include novel structures produced during the methods of the above aspects of the invention, including arrangements of bioparticles, immunoreagents, and sub-cellular constituents in the presence or absence of AC or DC electric fields.

Another aspect of the present invention is methods described for using active electronic matrix chip devices to produce electronically addressed arrays of capture immunoreagents. These methods generally comprise the sequential introduction of the capture immunoreagents (which are modified for attachment to the permeation layer at the microlocations) into the flow cell and electronically addressing the capture immunoreagents to the microlocations by electronically biasing the underlying electrodes.

Another aspect of the present invention is active electronic matrix chip devices with arrays of attached antibodies for use in the methods of the invention. These may be produced by the electronic antibody array construction methods of the invention. Alternatively, these may be produced by using mechanical deposition methods, prior to the enclosure of the active electronic matrix chip device in any closed fluid system (e.g., a flow cell as pictured in FIG. 1).

Another aspect of the present invention are methods for conducting electrophoretically-enhanced immunoreactions on active electronic matrix chip devices, as described herein, with or without DEP steps for bioparticle separation.

Still another aspect of the present invention are methods to lyse the desired cells isolated by DEP by applying at least one series of high-voltage DC pulses on the electrodes in a highly localized and controlled manner so that proteins and other cellular components are released from the cells in a manner which preserves their immunoreactivity.

Still another aspect of the present invention is perform one or more of the above operations, i.e., bioparticle/cell separation, cell lysis, immunoassay, and other bioassay processes in a self-contained flow chamber on a single chip.

BRIEF DESCRIPTION OF THE DRAWINGS

FIGS. 9A and 9B: 9A is a white light image of the microscale separation of *B. globigii* spores and heat-killed *E. coli* bacteria on the 5×5 array. The electrodes in the array were addressed with an AC voltage at 50 kHz and 5 V p—p. The spores and bacteria were suspended in a 280 mM mannitol solution having a conductivity of 20 µS/cm. 9B is a magnified view showing that the spores were collected on the electrodes and that the bacteria were repelled from the electrodes.

Incorporation of References

Figure 1:
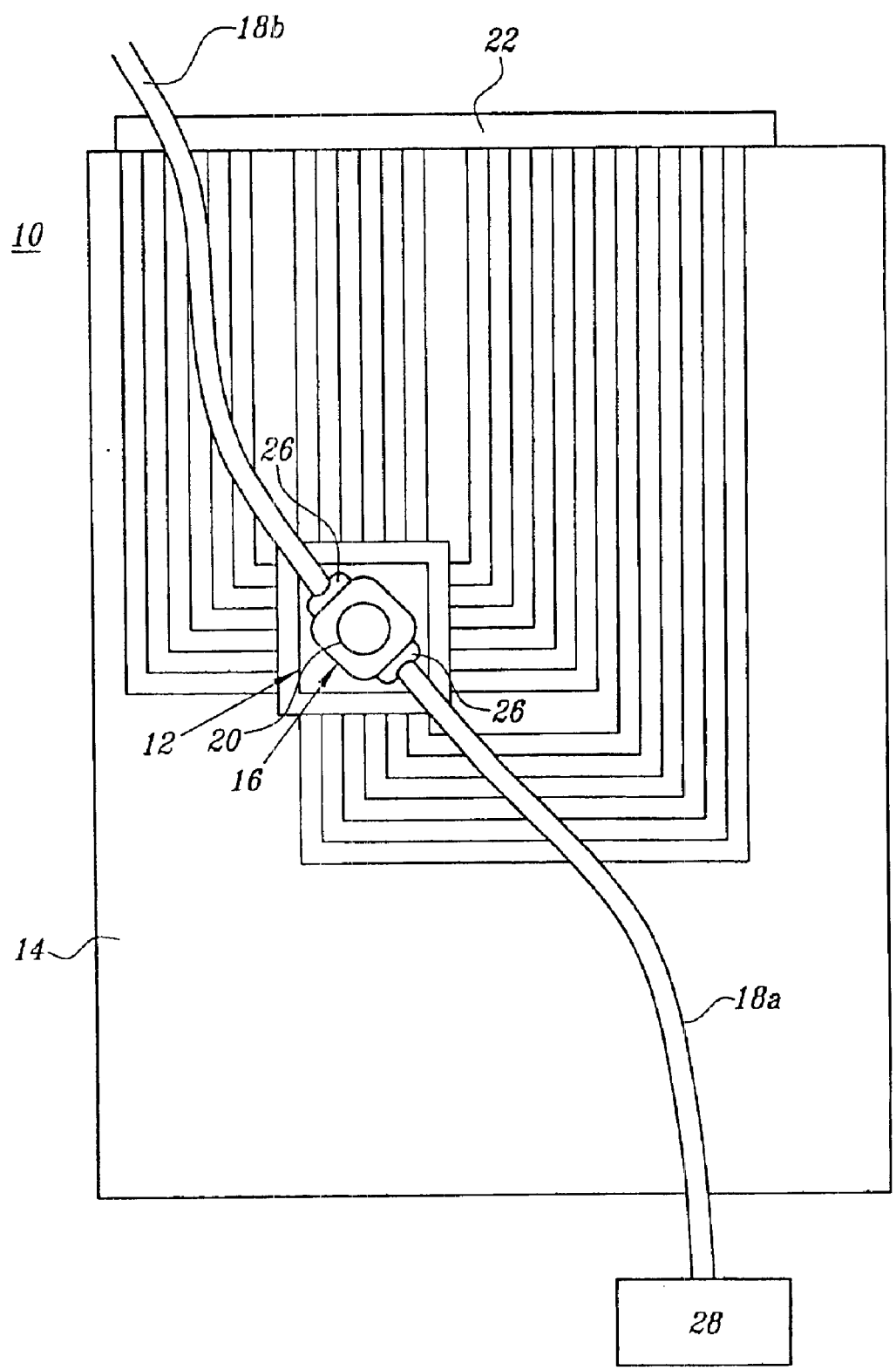
FIG. 1: A top view of a device for use in the present invention, bearing a microchip (12) and a flow chamber (16) including fluid tubing (18) and a detection window (20).

All patents, applications, and other references cited herein are incorporated herein as if reproduced herein in their entirety, and may be utilized to the full extent permitted to provide further support, description, and explanation for the invention described herein. Especially, the patents and other references referred to in describing the active electronic matrix devices and dielectrophoresis techniques on these devices are explicitly so incorporated so as to avoid undue duplication of information within this application.

DETAILED DESCRIPTION OF THE INVENTION

The present invention provides devices and methods for performing immunoreactions using capture and/or detection immunoreagents, dielectrophoresis for cell sorting and electronic lysis, immobilization of immunoreagents on electrodes via electronic addressing, DC high voltage-pulsed electronic lysis of cells, antibody capture of bioparticles or sub-cellular constituent antigens at the microlocations by electronic addressing, and detection of antigens from unknown samples, all of which can be conducted in a single system with one (or, optionally, more) active electronic matrix chip devices.

As used herein, "bioparticle" means any cell, virus, spore, pollen grain, liposome, or other biologically derived particle of a size which may be separated by dielectrophoretic techniques. Usually, these particles range in size from about 0.1 micron to about 100 microns in diameter. For comparison, most proteins, and also organelles or other cellular constituents, fall below this range. However, very large macromolecular complexes including proteins, lipids, biopolymers, and other components may reach sufficient size to be considered a bioparticle. The term bioparticle is used herein similar to "molecular species" in that it indicates several individual entities of the same type, or species. Bioparticles, plural, is used to indicate a plurality of bioparticle species.

As used herein "sub-cellular constituent" refers to a cellular component, including, but not limited to, proteins, proteoglycans, glycoproteins, glycosides, supramolecular complexes (comprising associated proteins, lipids, glycosides, biopolymers, etc) and organelles or organelle fragments. However, as used herein, the term "sub-cellular constituent" expressly excludes nucleic acids.

As used herein, the term "sample" denotes any biological sample which may contain a bioparticle of interest. Such samples may be taken or derived from firm biological tissues, blood, plasma, serum, ascites, lymph, sputum, stool, urine, or other biological fluids. Samples may also be derived from cell cultures or stocks. In addition, such samples may be derived from other sources such as food, water supplies, air quality samples, medical or research media, pharmaceutical products, or other sample sources for which a quality/contamination analysis may be desired.

Active Electronic Matrix Devices

The active electronic matrix forms the base for the compositions and methods of the invention. In general, the active electronic matrix devices utilized in the present invention consist of a planar substrate comprising an array of independently (individually) or semi-independently (in sets or groups) controlled electrodes. The array may be in any convenient geometric arrangement, including lines, radially symmetrical patterns, rectilinear grids, etc. One or more electrodes may be differently sized than the other electrodes in the array, and/or differently placed, in order to serve as a counter electrode or storage portion of the matrix device. The substrate and electrodes are covered by a permeation layer, which may be contiguous on the substrate, but which is at least above the microlocation electrodes of the array. This permeation layer is permeable to small ions, but protects the biomolecular reactants from the harsh electrochemical environment of the electrode. The area of the permeation layer above an electrode in the array forms a "microlocation."

Permeation layer materials may include any suitably permeable material, as have been described in the referenced patents. Particularly preferred materials include hydrogel type materials, including naturally derived physical hydrogels which comprise physically crosslinked biopolymers (e.g., agarose and its derivatives), as well as synthetic polymers hydrogels which are chemically crosslinked (e.g., acrylamide, methacrylamide, and other suitably hydrophilic synthetic polymer materials.) The permeation layer usually contains, at least on its surface at each microlocation site, reactive or binding moieties which allow the attachment of the capture immunoreagents. However, such attachment moieties may be absent if the active electronic matrix device is to be used only for the detection of DEP isolated bioparticles which adhere to the permeation layer due to their inherent chemical or physical properties. Typical permeation layer thickness ranges from about 0.5 to about 20 $\mu$m, more preferably in the range of about 1.0 to about 5.0 $\mu$m.

Active microelectronic chip/array technologies have been demonstrated which provide capability for selectively addressing arrays with nucleic acid sequences, carrying out rapid multiplex hybridization, and also providing electronic stringency for improving nucleic acid hybridization selectivity. These same basic microelectronic arrays can be used for the dielectrophoretic and immunological reaction methods and compositions of matter that are the subject of this invention. The basic designs and procedures for fabricating active electronic matrix chips and arrays, including devices with 25, 64, 100, 400, 1000 microlocations, and even density devices (10,000 microlocations), are described, for example, in U.S. Pat. No. : 6,017,696, entitled "Methods for Electronic Stringency Control for Molecular Biological Analysis and Diagnosis;" U.S. Pat. No. 5,605,662, entitled "Active Programmable Electronic Devices for Molecular Biological Analysis and Diagnostics;" and U.S. Pat. No. 6,099,803, entitled "Advanced Active Electronic Devices for Molecular Biological Analysis and Diagnostics," U.S. Pat. No. 5,632,957, entitled "Molecular Diagnostic Systems Including Electrodes;" and U.S. Pat. No. 5,849,486, entitled "Apparatus and Methods for Active Programmable Matrix Devices;" each of which is incorporated fully by reference herein.

In particular, those electronic stringency parameters (DC, AC/DC, and electronic pulsing protocols) which concern electronic perturbation, have been described in patents and applications which deal with the so-called area of fluorescent perturbation. See, e.g., U.S. Pat. No. 5,849,486, entitled "Apparatus and Methods for Active Programmable Matrix Devices." Additionally, the design and fabrication procedures for higher density microelectronic arrays (e.g., 400, 1200, 10,000, and higher numbers of microlocations) that have active on-board electronic control have been described in the above patents. Further information on the basics of electronic hybridization and stringency are also discussed in the following reference articles (Heller, M. J. , IEEE Engineering in Medicine and Biology, pp. 100–104, March/April 1996; Sosnowski, R., et al., Proc. Nat. Acad. Sci. 94, pp. 1119–1123, 1997; Edman, C. F., et al., Nucleic Acid Research 25, pp. 4907–4914, 1997; Cheng, J., et al., Nature/Biotechnology 16, pp. 541–546, June 1998; and Gilles, P. N., et al., Nature/Biotechnology 17, No. 4, pp. 365–370, 1999).

Figure 2:
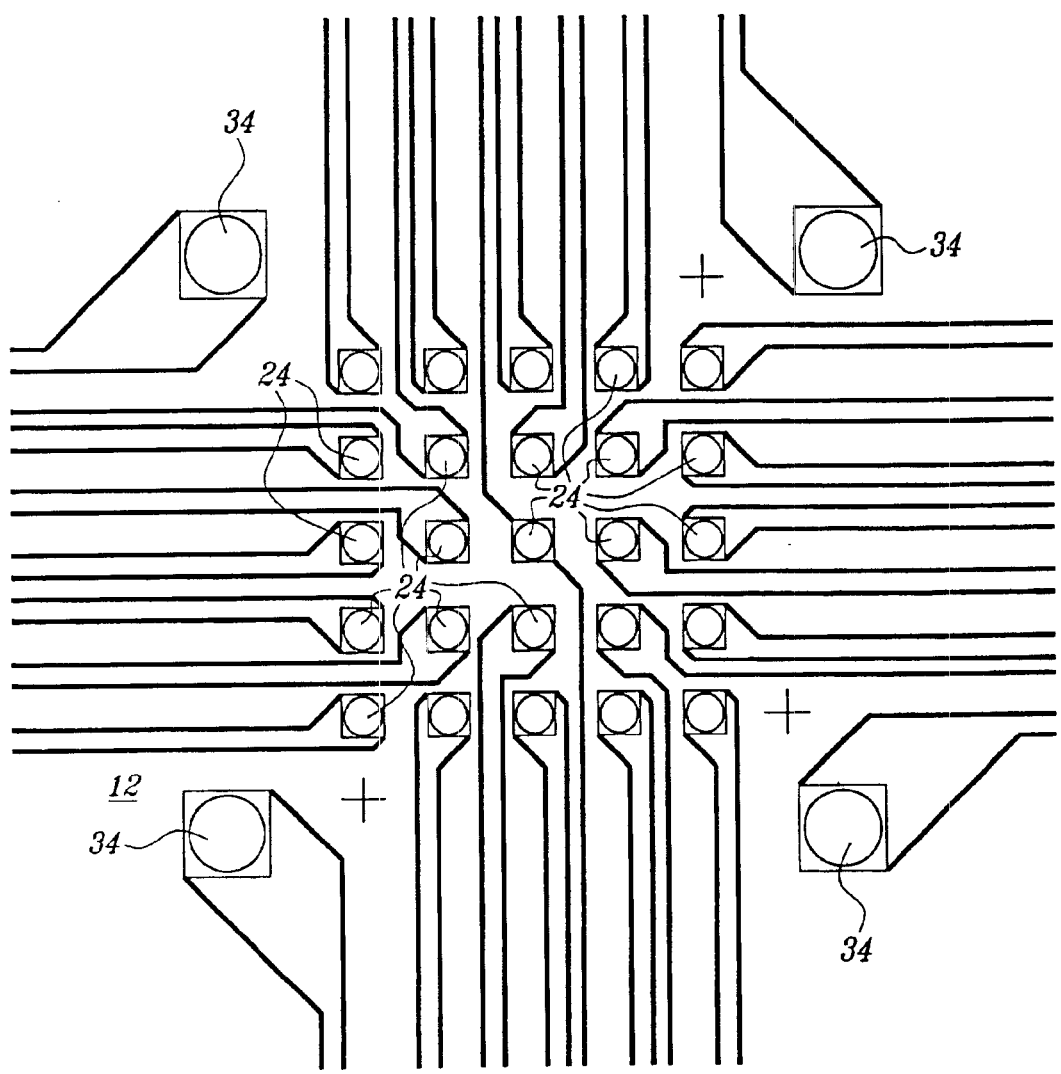
FIG. 2: A schematic view of a chip coated with a permeation layer (not shown schematically: in plane of figure) showing several circular microlocations electrodes (24) and four counter electrodes (34).
Figure 4:
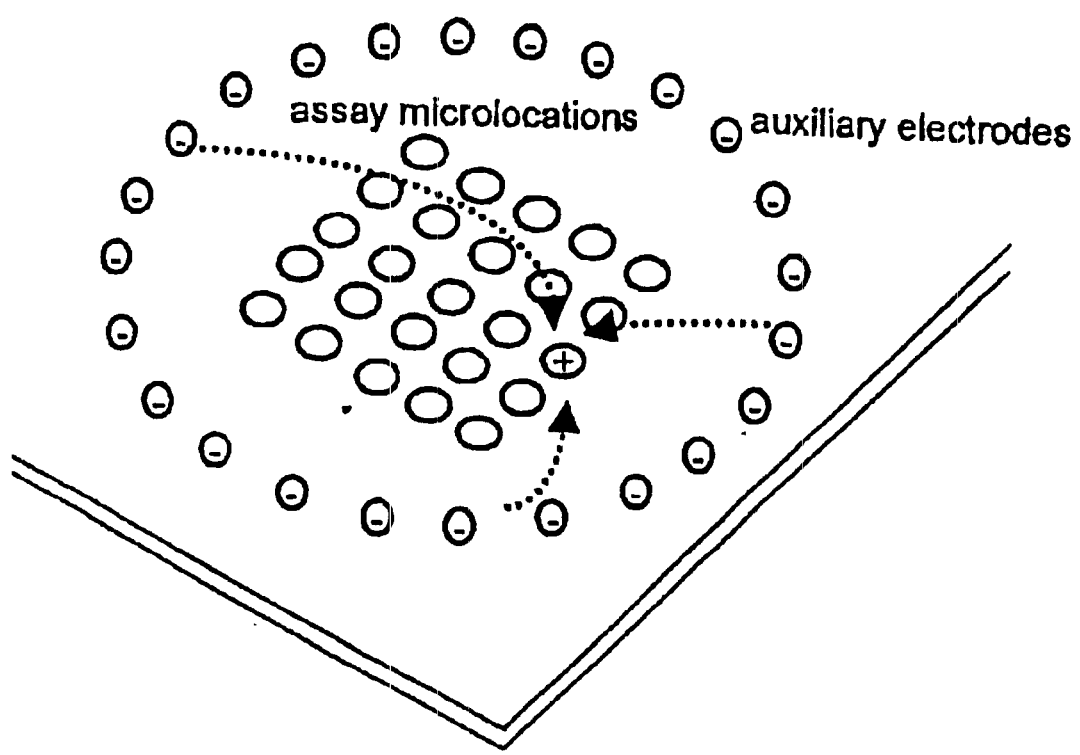
FIG. 4: An illustration of a 5×5 active electronic matrix chip, as used in the Examples. The microlocation electrodes, which are covered by a permeation layer, form a 5×5 array in the center of the chip. These are surrounded by a ring of counter electrodes (which may be bare). As an example, when addressing biotin-labeled antibodies to microlocations in an immunoreagent immobilization step, the ring of counter electrodes is biased negatively and the selected microlocation electrodes in the central array are biased positively to general an electric field. The field causes negatively charged proteins to move toward the positively biased microlocation electrodes in the central array. In the assay array, any number of microlocation electrodes can be biased at the same time to selectively attract proteins from solution to the microlocations.

Example devices are shown in FIGS. 1, 2, and 4. In one device embodiment for use in the present invention, the device comprises a cartridge 10, show in FIG. 1, including a microfabricated silicon chip 12 on a printed circuit board 14, a flow cell 16 mounted to the chip 12 to form a flow chamber including fluid tubing 18a and 18b and a detection window 20. The flow chamber preferably has a volume from about 5 to about 20 $\mu$l, more preferably from about 7 to about 10 $\mu$l. The cartridge 10 also includes output pins 22 for electronically connecting the cartridge 10 to an electronic controller (e.g. instrument or computer) (not shown).

An example microfabricated chip is shown in FIG. 2, and, as shown, includes a plurality of microelectrodes 24 and counter electrodes 34. The example chip 12 includes four counter electrodes 34, and five rows of five platinum microlocation microelectrodes 24, and is fabricated using standard semiconductor processing techniques that are well known. It should be noted that the number of electrodes could be more or less than that shown here, and that the present specification uses a five by five arrangement for illustrative purposes only and is not limited to the same. Indeed, a chip with more electrodes could facilitate recovery of a greater number of the targeted bioparticles and, therefore, a higher yield of nucleic acids. In addition, chips with larger numbers of microlocation electrodes could easily be divided into groups of microlocations dedicated to DEP separation and/or bioparticle analysis, and groups dedicated to immunoassay analysis of sub-cellular constituents. The center to center distance between neighboring electrodes 24 is preferably on the order of about 200 $\mu$l and the diameter of each electrode 24 is preferably on the order of about 80 $\mu$m.

In this embodiment, the chips 12 were prepared by first sputtering a titanium-tungsten (Ti—W) layer onto a thermally oxidized silicon wafer to a thickness of about 100 nm, and then sputtering a platinum layer to a thickness of about 300 nm on the Ti—W layer. A photolithographically defined wet etch in aqua regia was used to pattern the metalization. Thin films of low stress silicon nitride (1.3 $\mu$m) and silicon dioxide (100 nm) were deposited over the surface of the patterned metal by plasma-enhanced chemical vapor deposition. A photolithographically-patterned dry plasma etch was used to etch through the dielectric to create the exposed electrodes of the device. The chips 12 were each wire-bonded to a printed circuit board 14 (which preferably conforms to the person computer card standard of the Personal Computer Memory Card International Association).

After bonding the chips 12 to the circuit boards 14, the chips were washed with isopropanol followed by rinses with deionized water. The chips 12 were then blown dry by a stream of nitrogen. The boards 14 bearing the dried chips 12 were then placed vertically in a plasma cleaner boat and cleaned in argon (250 mTorr, 250 W) for five minutes. After the plasma cleaning, a permeation layer was added to each chip 12.

An example permeation deposition would proceed as follows: A 2,5% bottom permeation layer solution of glyoxyl agarose is prepared. Glyoxyl agarose (250 mg) (from Sigma, St. Louis, Mo.) is added to 10 ml of deionized distilled water, mixed, and then boiled for eight minutes. The completely dissolved agarose solution is hot filtered into pre-warmed (65° C.) Eppendorf tubes using a 1.2 $\mu$m syringe filter. The filtered agarose solution is equilibrated to 65° C. for five minutes. A streptavidin solution is prepared by suspending streptavidin (Boehringer Mannheim, Indianapolis, Ind.) in a solution containing sodium chloride (250 mM) and sodium phosphate (10 mM, pH 7.2). The streptavidin solution is combined with the temperature equilibrated agarose solution to yield 2% agarose and 1 mg/ml streptavidin. The warm solution (50 $\mu$l) is placed on the chips and spun in a spin-coating apparatus at about 10,000 rpm for twenty seconds at room temperature. The coated chips are then baked at 37° C. for thirty minutes.

The example cartridge 10 of the present invention was completed by selecting a prepared chip 12/printed circuit board 14 and gluing a polycarbonate molded flow cell 16 onto the chip 12 preferably using a UV adhesive (Norland 68, Thorlabs, New Brunswick, N.J.) under a 200 W UV light for forty-five seconds (4 Joules/cm$^2$). A cover glass slip may glued on top of the flow cell 16 to form a sealed flow chamber using the same procedure, or the flow cell may include a preformed window. Input and output plastic tubing 18a and 18b, respectively, were added to the in-port and out-port of the flow cell 16 via lure fittings 26 and then glued in place.

Dielectrophoretic Methods on Active Electronic Matrix Devices

Bioparticle Separation and Manipulation

Various advanced devices for nucleic acid analysis utilizing dielectrophoretic separation of bioparticles are known. Cheng et al., U.S. Pat. No. 6,071,394, and U.S. Pat. No. 6,280,590, entitled "Channel-Less Separation of Bioparticles on a Bioelectronic Chip by Electrophoresis" describes a system and method for performing active molecular and biological sample preparation and diagnostic analysis of nucleic acids by dielectrophoresis on a bioelectronic chip. These patents are explicitly incorporated by reference.

The basic theory of dielectrophoresis, motion of particles with induced polarization under non-uniform electric field, has been extensively studied. See, e.g., R. Pethig, "Dielectrophoresis: Using Inhomogeneous AC Electrical Fields to Separate and Mutate Cells," Crit. Rev. Biotech, 16:331–48 (1996); X, Wang, et al., "A Unified Theory of Dielectrophoresis and Travelling Wave Dielectrophoresis," J. Phys. D: Appl. Phys., 27: 1571–74 (1994); G. Fuhr, "Cell Manipulation and Cultivation Under AC Electric Field Influence in Highly Conductive Culture Media," Biochim. Biophys. Acta 1158:40–46 (1993); and M. Washizu, "Molecular Dielectrophoresis of Biopolymers," IEEE Trans. Industry Applicat. 30:835–43 (1994). The dielectrophoresis phenomenon can be generally described by energy potential $$\psi = \overline{m} \cdot \overline{E}$$

where $\overline{m}$ is the induced dipole moment of a particle suspended in dielectric medium and $\overline{E}$ is the applied electric field. Therefore, the dielectrophoretic force acting on a particle can be written as a gradient of energy potential.

When the particle has zero net charge and the surrounding medium is isotropic, the average energy potential can be simplified as $$\psi = -(1/2)pvE^2$$

where p is the effective polarizability of the suspended particle with volume v. The value and sign of polarizability (p) depends on the permittivity of particle and medium, as well as the frequency of the applied electric field. R. Pethig, "Dielectrophoresis: Using Inhomogeneous AC Electrical Fields to Separate and Manipulate Cells," *Crit. Rev. Biotech.*, 16:331–48 (1996). At a steady state, the particle with positive polarizability (p>0) will stay at the low field region.

To model the distribution of the electric field around the electrodes 24 of the present invention, the following two assumptions were made: First, within the low frequency range the dimensions of both chip and flow chamber are much smaller than the wavelength of the applied AC field. Second, the sample solution has electroneutrality. Under these two assumptions the electric field can be calculated for a particular addressing configuration in the present experiment set-up by solving Laplace's equation $$\nabla^2 \phi = 0 \text{ and } \bar{E} = -\nabla \phi$$

($\phi$ is electric potential) with boundary conditions of fixed voltage on electrodes and zero normal current on the rest of the surface, $\phi = V_0$ at positive electrodes, $\phi = 0$ at negative electrodes, and $\delta\phi/\delta n = 0$ at the rest of the chip surface and the flow chamber.

The electric field in the sample solution, and, therefore, the energy potential of polarized particles, is numerically calculated by the finite-difference method. See, K. Binns, "The Analytical and Numerical Solution of Electric and Magnetic Fields" (John Wiley & Sons, N.Y. 1992).

The frequency at which the biopatticles in a sample may be separated (i.e., the desired biopatticle is subject to negative or positive dielectric force) can also be empirically determined using routine experimentation. For example, the biopatticle mixture may be subjected to different frequency and medium conductivity conditions, using a gradually increasing sinusoidal signal (10 volts, peak to peak) starting from about 5 KHz.

Figure 3A:
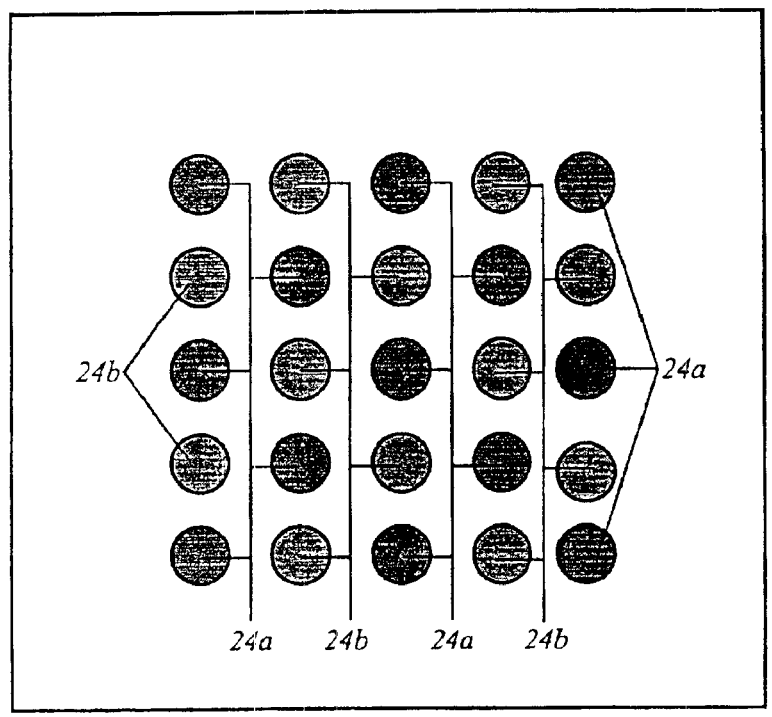
FIGS. 3A to 3D: 3A is a schematic illustration of checkerboard style electronic addressing of a five by five arrangement of circular electrodes where each electrode has opposite biasing as its nearest neighboring electrodes, groups 24a and 24b (the use of the 5×5 arrangement is for illustrative purposes only, the array can have more or less than 25 electrodes). 3B is a computer model illustration of the AC field distribution corresponding to the checkerboard style addressing shown in 3A, where a regular distribution of electric field is obtained with the field maxima at each electrode and the field minima in the areas between the electrodes. 3C is a schematic illustration of square wall style electronic addressing of a five by five arrangement of circular electrodes where electrodes on the same square frame have the same biasing which is opposite from those electrodes on the nearest neighboring square frame(s) (groups 24a and 24b). 3D is a computer model illustration of the AC field distribution corresponding to the square wall style addressing shown in 3C.
Figure 3B:
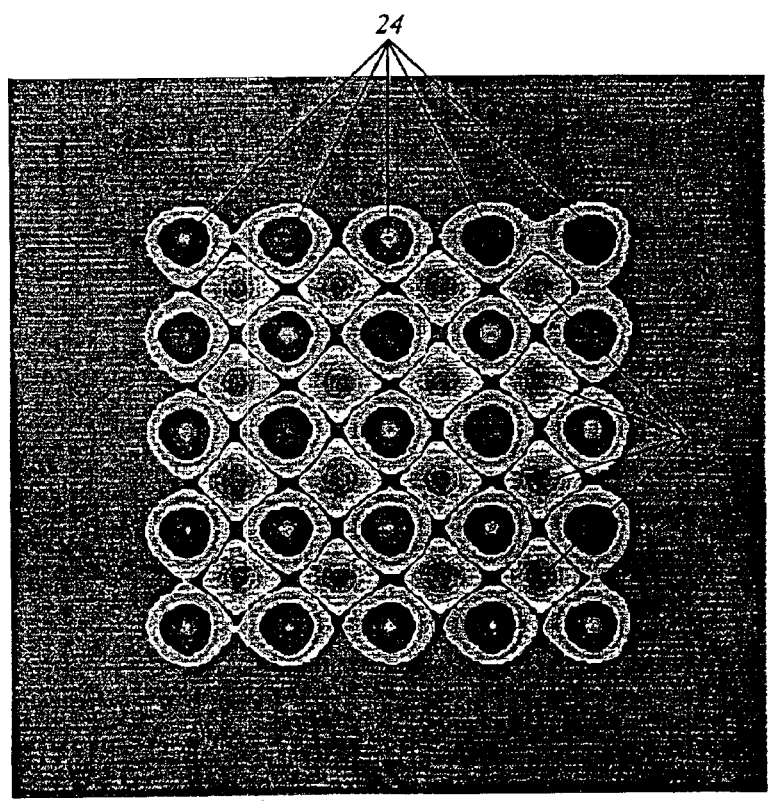
Figure 3C:
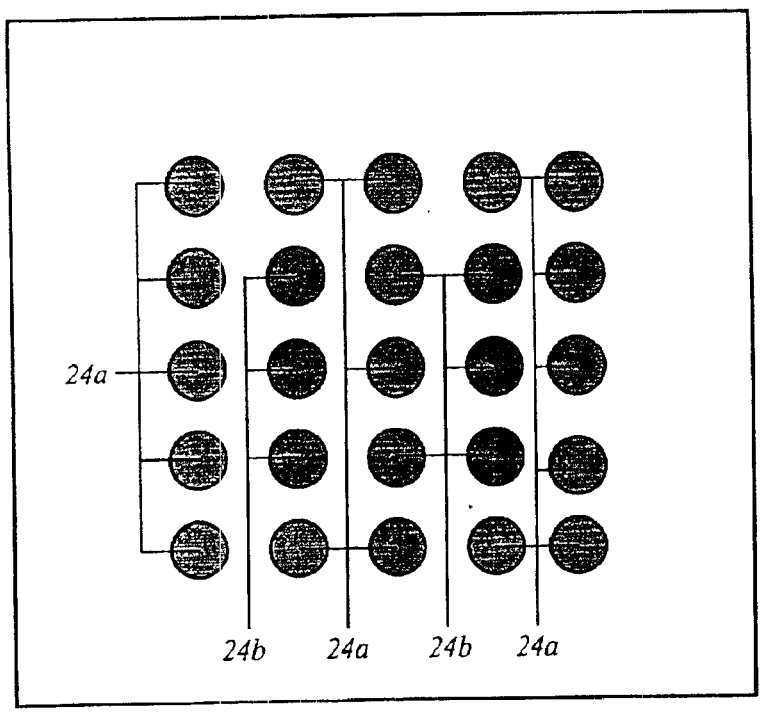
Figure 3D:
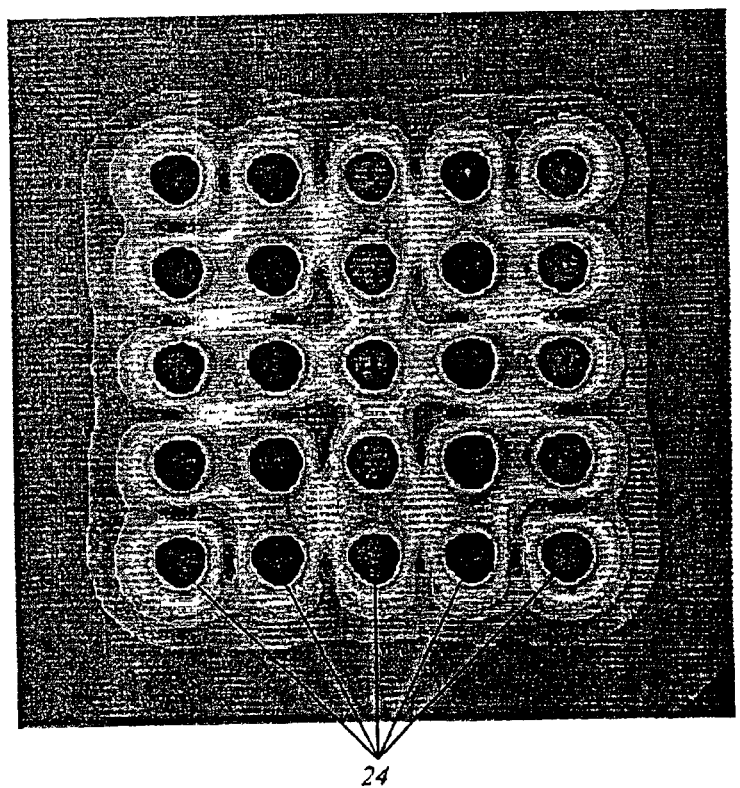

Several biasing formats may be devised to produce suitable areas of low and high AC field strength. For example, the checkerboard shown in FIG. 3A may be used. As is shown in FIG. 3B, the field distribution corresponding to the checkerboard style addressing provides a uniform distribution of the electric field with the electric field maxima at each microlocation electrode and field minima in the areas between the microlocations. In comparison, the square wall style addressing (shown in FIGS. 3C and 3D) does not provide field minima interspersed between electrodes. Having an arrangement where the field minima are interspersed between electrodes is preferred because with such an arrangement washing off undesired cells (e.g., those collected in the areas of field minima) is easily accomplished without disturbing the desired cells (i.e. those retained on the electrodes), as the desired cells and electrodes do not stand in the way of fluidic flow and, hence, do not block the washing off flow containing any undesired cells. It should be understood that the checkerboard style addressing could essentially be accomplished by grouping electrodes and having each group of electrodes biased opposite from its nearest neighboring groups of electrodes. Additionally, if the biopatticles of interest collect at the AC field minima, a biasing pattern may be designed to allow collection of the biopatticles over non-biased microlocations for immunoimmobilization by capture immunoreagents.

As shown in Example 4, the microscale separation described exploited the opposite DEP forces exerted on the two types of biopatticles under appropriate separation conditions (e.g. the frequency of the applied field, the electrical conductivity of the solution). The performance of such separations is dependent on the dielectric properties of the biopatticles to be selectively manipulated. Wide distribution in biopatticle dielectric properties may result in individual biopatticles of the same type exhibiting opposite DEP effects, leading to a noncomplete separation of the biopatticles on the chip. With known dielectric properties and their distributions for the biopatticles, it is possible to analyze the separation performance. Because the dielectric properties of *B. globigii* spores used in Example 4 were unknown at the time, such a theoretical analysis was not performed and the applied field frequency for the separation was empirically discovered.

Immunological Reaction Components

As used herein, "immunoreaction" or "immunological reaction" generally refers to a specific binding reaction between an antibody, or antibody-like molecule, and an antigen, or an epitope-bearing molecule, in addition to further specific binding interactions utilized to detect the antigen-antibody immunoreaction complex. In general, the immunological reactions will be described in terms of three types of components: binding or capture components, analyte components (which may include, for example, an entire bacterial cell, or merely a protein toxin antigen from a lysed cell), and detection or labeling components. These are the basic components of most immobilized immunoassay formats, including traditional sandwich and competitive binding assay formats. In the case of sandwich formats, the immunoreaction complex may include one or more layers of labeling components in order to generate a signal to detect the presence of the analyte in the sample. In the case of competitive immunoassay formats, a known amount of the analyte itself is labeled, and the extent of the binding of this labeled analyte in the presence, and absence, of the sample is determined. Any of the traditional immunoassay formats, including sandwich and open-sandwich formats (as used in the Examples), competitive binding formats, and others, may be utilized in the present invention.

For the purposes of this invention, an "antigen" is a molecule which presents an immunochemically reactive entity which presents antigenic determinants which comprise a particular spatial arrangement of atoms which is recognizable by an antibody, or an "epitope." Antigenic molecules which induce an immune response are usually quite large. Many antigens are proteins, polypeptides, polysaccharides, proteoglycans, glycoproteins, lippopolysaccharides, and other biologically derived macromolecules (which may be subcellular constituents). Bioparticles such as cells, bacteria, or virus, and also larger sub-cellular constituents such as cell surface membranes, cell surface proteins, cell surface receptor and effector sites, organelles, nuclei, mitochondria, ribosomes, synthetic micelles, and other natural or synthetic surfaces also present epitopes which can be recognized by antibodies, usually in the form of a molecular portion of the overall structure. However, the epitope recognized by an antibody is usually a small structure, and only a portion of the whole antigen. Thus, the molecules of "antigens" also comprise smaller portions of a naturally occurring antigen which contain an epitope (e.g., periodate digested bacterial polysaccharides), as well as synthetic molecules (peptides, polysaccharides, etc.) which have been designed to mimic an epitope. For convenience, these molecules will be referred to throughout as "antigens," although this usage of the term understood to encompass all of the epitope-bearing molecules described above.

As referred to herein, an "antibody" is a structure that has specific affinity for an epitope. These include any multiple polypeptide chain-containing molecular structure that has a specific shape which fits to and recognizes an epitope, where one or more non-covalent binding interactions stabilize the complex between the molecular structure and the epitope. The specific or selective fit of a given structure and its specific epitope is sometimes referred to as a "lock and key" fit. The archetypal "antibody" molecule is the antibody, and all types of immunoglobulins (IgG, IgM, IgA, IgE, IgD), immunoglobulin fragments comprising the binding site (i.e., Fab', papain, pepsin, or ficin fragments), derivatized immunoglobulins (with added chemical linkers, detectable moieties [fluorescent dyes, enzymes, substrates, chemiluminescent moieties], specific binding moieties [such as streptavidin, avidin, or biotin], etc.), recombinant immunoglobulins, single-stranded engineered immunoglobulins and humanized or hybrid immunoglobulins. "Antibodies" also may include artificial antibody-like molecules, such as the triad-peptide "finger" constructs described in WO 01/13126, entitled "Microelectronic Molecular Descriptor Array Devices, Methods, Procedures, and Formats for Combinatorial Selection of Intermolecular Ligand Binding Structures and for Drug Screening," or analogs thereof. For convenience, the term "antibody" will be used throughout to generally refer to these molecules, although the term will encompass all immunoglobulins, derivatives, fragments, and modifications as described above.

As referred to herein, "immunoreagents" are molecules comprising an antibody, as defined. Capture immunoreagents generally comprise moieties for attachment to the permeation layer of an active electronic matrix device. These may include, for example, moieties for non-covalent attachment, such as biotin, streptavidin, avidin, other biotin binding proteins, phenyl boronic acid (PBA), salicylhydroxamic acid (SHA), or synthetic binding systems such as those described using pyranosyl RNA or necleo-delta-peptides (CAN) in WO 01/13126. Of these, biotin and synthetic binding system moieties are particularly preferred. Or, these may include moieties for covalent attachment, such as hydrazides, hydrazines, amines, aldehydes, acids, active succinimidyl esters, maleimides, etc. Of these, hydrazides and hydrazines are particularly preferred.

Immunoreagents may also be detection immunoreagents which have been detectably labeled with one or more moieties for detection. Distinguishably detectable labeling moieties, detectable moieties, or reporter group(s) for use in the inventions are preferably fluorophores. However, also suitable are chromophores, biotin/avidin detection systems (if biotin/avidin is not utilized to immobilize capture Immunoreagents), chemiluminescent agents (such as acridinium), enzymes, gold particles, magnetic beads, metal chelates, radioisotopes, other antibodies, and nanoparticles. Suitable fluorophores include active-ester or other reactive derivatives of $BODIPY_{630/650}$ X-SE, Texas Red X-SE, or BODIPY TRX-SE, Cy-dyes, fluorescein, rhodamine, phycoerythrin, Lissamine, and coumarin, and Alexa dyes.

Several methods of detecting such fluorescently labeled immunoreaction components in immobilized array formats are well known in the art, as are methods for detecting other types of reporter groups. Excitation/detection equipment that is able to rapidly gather fluorescence data from microarrays with 100, 400, 1000, and over 10,000 test sites in very dense packing arrangements has been described in U.S. Pat. No. 6,309,601, entitled "Scanning Optical Detection System," and is suitable for use in the methods of the invention.

Immunoreagent and Sub-Cellular Constituent Transport to and Immobilization at Microlocations of Active Electronic Matrix Devices In order to electrophoretically transport toxin proteins and immunoreagents for immunochemical reactions, the isoelectric points of these proteins should be known and the pH of the addressing conditions adjusted, if necessary, to determine the direction that each protein (or other sub-cellular constituent) on the device will travel in the applied electric field. Isoelectric points may be measured using a variety of techniques well known in the biochemical arts. From the isoelectric point, the polarity of the reagents at pH 7.5 in 50 mM histidine (a buffer of choice for electrophoretic transport on active electronic matrix devices) may be deduced. Although 50 mM histidine is the buffer of choice, other low-conductivity buffers at other pHs may be used when necessary to ensure that the immunoreagent or sub-cellular constituent will migrate towards the biased electrode. In the examples, buffers and pHs have been chosen so that the immunoreagents and toxins are negatively charged, and migrate towards a positively biased electrode in an applied DC field. However, persons of skill in the electrophoretic arts may easily modify the described addressing conditions to accommodate proteins or other sub-cellular constituents which are positively charged.

Although any of the above mentioned attachment chemistries could be utilized with the appropriately formulated and prepared permeation layer (e.g., a hydrazide derivatized antibody attachment to an active succinimidyl ester containing permeation layer), biotin attachment shall be discussed specifically herein, as streptavidin-containing permeation layers are commonly utilized in the examples. Any number of combinations of microlocations can be biased negative, positive, or neutral with direct current (DC) to create the desired electric field on the chip array. An array of capture antibodies is easily created by successively placing solutions of a specific biotinylated antibody on the chip and electrophoretically transporting them to the desired microlocation by appropriately biasing the electrode under the microlocation. An antibody becomes immobilized at the desired microlocation through the stable non-covalent binding interaction between biotin and streptavidin in the permeation layer covering the electrodes. The active electronic matrix device is then ready to be utilized in the immunoreagent capture methods described herein.

As will be appreciated by those of skill in the art, the placement of capture immunoreagents on the active electronic matrix device will depend on the format of the assay in which the device will be used. For instance, where the desired bioparticles (e.g., bacterial cells, spores, or viruses) are to be collected in high-field regions, the capture immunoreagents would be immobilized at the microlocations whose electrodes will be used to generate the AC field. Conversely, if the desired bioparticles are to be collected in low-field areas, the capture immunoreagents would be immobilized at microlocations located within the expected low-field areas between microlocations whose electrodes will be used to generate the AC field. In some embodiments, such capture immunoreagents could be immobilized by mechanical application between microlocations prior to the sealing of the active electronic matrix device within a flow cell for later passive immunoreaction labeling (e.g., between the microlocations where a checkerboard biasing pattern is to be used.) However, it is preferred to design the biasing pattern so that microlocations are located in the low-field areas (which could be easily accomplished in a concentric square pattern, for instance), so that the microlocations may be later used to electrophoretically transport detection immunoreagents to the microlocations containing the captured bioparticles.

If proteins, organelles, or other immunologically reactive analytes from lysed bioparticles collected by DEP techniques are to be detected using electrophoretically enhanced immunoassay techniques, as described below, then several options exist for placement of the capture immunoreagents for the assay. The capture immunoreagents may be immobilized at the microlocations where the bioparticles to be lysed are to be gathered, or at other microlocations which may or may not be part of the portion of the array utilized in the DEP separation. For example, in a 10 by 10 array of microlocations where a 5 by 5 corner section is to be utilized for DEP, the capture immunoreagents for the sub-cellular analyte immunoassay may be immobilized on microlocations in an adjacent section of the array. Or, alternatively, another active electronic matrix device may be used within the same flow cell for this purpose, or within another fluidly connected flow cell. Such arrangements are described in U.S. Pat. Nos. 6,280,590 and 6,071,394, referenced and discussed above.

In the Examples, capture and detection immunoreagents were addressed in 50 mM histidine, 7.5 pH, to their microlocations at concentrations between about 100 nM and 500 nM, at about 200 to 500 nA per microlocation for about 1 minute, optionally with a repeat round of addressing under the same conditions. These conditions may be generally applied and optimized for the addressing of particular capture and detection immunoreagents for use in a particular application of the methods of the invention.

Similarly, in Example 2, fluorescein modified toxins were addressed in 50 mM histidine, pH 7.5, to capture microlocations at 100 nA per microlocation for about 1 minute. For similarly sized and charged sub-cellular constituents to be assayed in the methods of the invention, similar addressing parameters may be utilized (e.g., 50 to 500 nA over 0.5 to 5 minutes.) In general, however, the electrophoretic mobility and approximate expected concentration, and other interfering considerations (e.g., competitive binding with other sub-cellular components or proteins in the sample) particular to the protein or sub-cellular constituent to be analyzed should be taken into account when modifying the amperage or time used for addressing the analyte species. In general, increases of amperage and/or time may be appropriate in situations where the protein has low electrophoretic mobility, or is present at low concentrations. However, one should keep the addressing time frame in the range of several seconds to several minutes, in order to avoid increased background from non-specific binding.

Immunochemical Immobilization and Detection of Bioparticles on Active Electronic Matrix Devices As described above in the dielectrophoresis discussion, and shown in Example 4, bioparticles may be separated to predetermined areas of low or high AC field strength on the active electronic matrix chip devices by applying an AC current through the microlocation electrodes. By utilizing immunoreagents in detection and/or capture roles, the sensitivity, specificity, and usefulness of this technique can be greatly improved.

Some bioparticles have inherent "sticky" properties (e.g., the *B. globigii* spores), and can adhere non-specifically to the permeation layer surface due to their chemical or physical properties. When the active electronic matrix array microlocations are biased in a pattern so that areas of expected aggregation of the bioparticles in the AC field are at microlocations of the device, the bioparticles may be collected at "aggregate" microlocations. This is most easily accomplished for bioparticles which migrate to high field strength areas, as these naturally lie on the biased microlocations. However, by careful design of the biasing pattern, aggregate microlocations lying in low field areas may also be provided. After DEP isolation of "sticky" bioparticles, the aggregate microlocations may be used for immunodetection of the bioparticles. By introducing a solution of detection immunoreagent specific for the bioparticle (e.g., a fluorescently labeled polyclonal goat antibody), and biasing the aggregate microlocation electrode to eletrophoretically transport the detection immunoreagent to the aggregate microlocation, as described above. After the detection immunoreagent has bound to the bioparticle at the microlocation, and optionally washing unbound immunoreagent from the device, the presence of the bioparticle on the microlocation may be detected by detecting the label on the immunoreagent. Optionally, if a concentration standard curve is established with known concentrations of the bioparticle, the technique can also be used to quantify the amount of immobilized bioparticle at the microlocation. Although the bioparticle on the aggregate microlocation may be detected by non-electrically mediated labeling techniques, such as cell dye stains or passive incubation with the detection immunoreagent according to traditional immunoassay procedures (e.g., the confirmation assay of Example 2D), the methods of the invention provide the advantages of decreased time of assay and increased specificity over the traditional techniques.

In cases where the bioparticle is not inherently "sticky", capture immunoreagents may be utilized to enhance the retention and immobilization of the bioparticles during and after the DEP process. If a capture immunoreagent specific for the bioparticle (e.g., a biotinylated mouse monoclonal antibody specific for *S. auraleus*) is immobilized at the aggregate microlocation, bioparticles aggregating at the microlocation during the DEP process will be specifically and firmly retained at the microlocation. Thus, the isolated bioparticles may retained during more vigorous washes to remove unwanted sample constituents, without maintaining the AC field. The immunoimmobilized bioparticle may then be preferably detected on the aggregate microlocation by an eletrophoretically enhanced detection immunoreaction, as described above. Alternatively, the bioparticle may be detected utilizing traditional passive techniques.

It should be noted that this immunoimmobilization technique may also be utilized by attaching capture immunoreagents to the permeation layer between the microlocations which are biased in the DEP process (e.g., in the checkerboard format shown in FIGS. 3A and 3B) in order to retain bioparticles which migrate to low AC field strength areas at those positions. However, this embodiment is not preferred, as eletrophoretically enhanced detection cannot be utilized (due to the lack of an underlying electrode), and traditional passive detection techniques must be utilized.

Immunodetection of Sub-Cellular Antigens in Immunoassay Formats on Active Electronic Matrix Devices after Dielectrophoretic Separation and/or Lysis of Bioparticles Once a cell bioparticle is immobilized or isolated on the active electronic matrix chip device, as described above, it may be lysed to release sub-cellular constituents for detection. Electronic lysing on the active electronic matrix chip devices may be easily accomplished by subjecting the cells to a series of high voltage pulses. Such electroporation lysis techniques are generally known in the arts. With reference to FIG. 2, with cells immobilized on a group of microlocations with underlying electrodes 24, the series of electric pulses may be applied by oppositely biasing the microlocation electrodes and the counter electrodes 34 at an appropriate voltage for an appropriate period of time. For example, *E. coli* on microlocation electrodes was lysed using pulses of 500 V, 50 $\mu$s pulse width, changing the polarity every twenty pulses between the two groups of electrodes. A total of 400 pulses were utilized for the lysis process. Similar conditions may be utilized to lyse other cells, with minimal optimization.

The ease of detection of a sub-cellular antigen will depend on the form of the antigen in sample (e.g., complexed with other constituents, general size, overall charge, and electrophoretic mobility.) The preferred forms of antigen include soluble proteins, as illustrated in Example 2. These types of sub-cellular constituents may be eletrophoretically transported and immobilized by capture immunoreagents on a microlocation in a very short time period. Therefore, the preferred embodiments of the invention focus on, but are not limited to, soluble protein immunodetection.

Once the cell bioparticles have been lysed, the sub-cellular constituent of interest (preferably a protein) may be eletrophoretically transported (or addressed), as described above, by biasing the electrode under a "capture" microlocation with an attached capture immnunoreagent specific for the sub-cellular constituent. After binding to the capture immunoreagent, and optionally washing the active electronic matrix chip device to remove unbound sub-cellular constituents the sub-cellular constituent may be detected by addressing a detection immunoreagent specific for the sub-cellular constituent to the microlocation. After the detection immunoreagent has bound to the sub-cellular constituent at the microlocation, and optionally washing unbound immunoreagent from the device, the presence of the sub-cellular constituent on the microlocation may be detected by detecting the label on the immunoreagent. Optionally, if a concentration standard curve is established with known concentrations of the sub-cellular constituent, the technique can also be used to quantify the amount of immobilized sub-cellular constituent at the microlocation.

Alternatively, the sub-cellular constituent may be detected by other means, such as non-specific labeling prior to introduction onto the active electronic matrix device comprising the capture microlocation (e.g., fluorescein isothiocyanate labeling as described in Example 2), radioactive metabolism trace labeling in the cell bioparticle, or by traditional passive immunodetection techniques. Although the preceding describes a traditional sandwich immunoassay format, other immunoassay formats (e.g., competitive binding) could be adapted for use with the eletrophoretically enhanced immunoassay methods in a similar manner. In addition, although the assay is described here in conjunction with a DEP process, the eletrophoretically enhanced immunoassay could be utilized as a stand alone assay for detecting proteins or other biomolecules in sample mixtures, as supported by Example 2.

EXAMPLES

The following examples are offered to further illustrate the various aspects of the present invention, and are not meant to limit the invention in any fashion. Based on these examples, and the preceding discussion of the embodiments and uses of the invention, several variations of the invention will become apparent to one of ordinary skill in the art. Such self-evident alterations are also considered to be within the scope of the present invention.

Example 1

Active Electronic Matrix Chip Devices Used in the Experiments

Active electronic matrix chips (like those pictured in FIG. 6), designated as the '5×5 array', were fabricated on silicon wafer using semiconductor processing technique. The 5×5 array chip consisted of 25 circular, platinum electrodes that were 80 $\mu$m in diameter on a 200 $\mu$m center-to-center spacing and covered an area of 0.88×0.88 mm$^2$, with reference electrodes surrounding the center array. Other areas on the chip were used for the connection pads to external signal sources and for electric wires between 5×5 array to these pads. An approximately 1 $\mu$m agarose permeation layer that contained streptavidin was prepared on the 5×5 array chip using a spin-coating technique.

The chip cartridge was formed by wire binding of the chip to a printed circuit board and was assembled with a flow cell (similar to that pictured in FIG. 1). A polycarbonate molded flow cell and a cover slip were attached to the chip with a UV-cured adhesive to form a sealed chamber. The flow cell was built over an area of 4.10×4.10 mm$^2$ covering the electrode-containing area of the chip and had about 7.5 $\mu$l volume with a thickness of 450 $\mu$m. Input and output fluidic adapters were formed by plastic tubing with a luer fitting, and were inserted and sealed into the flow cell. A peristaltic pump (model RP-1, Rainin Instruments, Woburn, Mass.) was connected to either input or output tubing of the cartridge for sample introduction and washing protocols. All experiments except the immunoassay for *E. coli* were performed on chips with flow cells.

The electronic connections for the cartridge were accomplished through a home-built switch box that addressed electrical signals to individual electrodes. The AC signals were provided by a signal generator (model HP33120A, Hewlett-Packard, Santa Clara, Calif.). The DC current was supplied by a Keithley 236 Source Measurement Unit (Keithley Instruments, Cleveland, Ohio) through a CMOS (complementary metal-oxide semiconductor) switch multiplexer.

Example 2

Immunoassays on Active Electronic Devices for Bacterial Toxin Proteins

2A: Modification and Determination of Isoelectric Points for Antigens to be Assayed Staphylococcal enterotoxin B (SEB) and cholera toxin B (CTB), as well as fluorescein labeled CTB, were obtained from Sigma (St. Louis, Mo.). SEB toxin was modified with fluorescein isothiocyanate. The fluorescein labeling of the toxins allowed for direct visualization in a capture immunoassay without adding a secondary detection step. Analyte derivatization (e.g., with a non-specific label such as fluorescein isothiocyanate) has proven practical in other assay contexts, and could be incorporated into a single-device format by utilizing a reaction chamber in between fluidly connected DEP preparation and immunoassay areas of a closed active electronic matrix chip device. Isoelectric points for the modified and unmodified toxins were determined by isoelectric focusing using pH 4–10 NOVEX IEF gels (Invitorgen, Carlsbad, Calif.).

SEC was modified to an extent of 2 mol fluorescein per mole of toxin. CTB was modified to an extent of 5 mol fluorescein per mole of toxin. Fluorescein isothiocyanate modifies protein lysine groups and in doing so forms a thiourea derivative of lysine. Upon fluorescein modification, there is loss of a positive charge from lysine and the addition of two negative charges on fluorescein with pKa values of 4.3 and 6.4. The net change in charge at pH 7.5 is approximately −3 units for each fluorescein added.

Prior to modification, SEB focused to a band with a pI of 8.3, and CTB focused to a band with a pI of 8.0. Fluorescein modification lowered the pI of SEB significantly; several bands with pI between 5.2 and 6.5 were observed on the gel. Modification of CTB with fluorescein also showed multiple bands with a lower pI between 5.8 and 6.3. The magnitude of the change in charge for a protein modified with only three fluorescein group underscores the importance of evaluating the charge profile of a protein prior to using it in an electric field driven assay.

Figure 5:
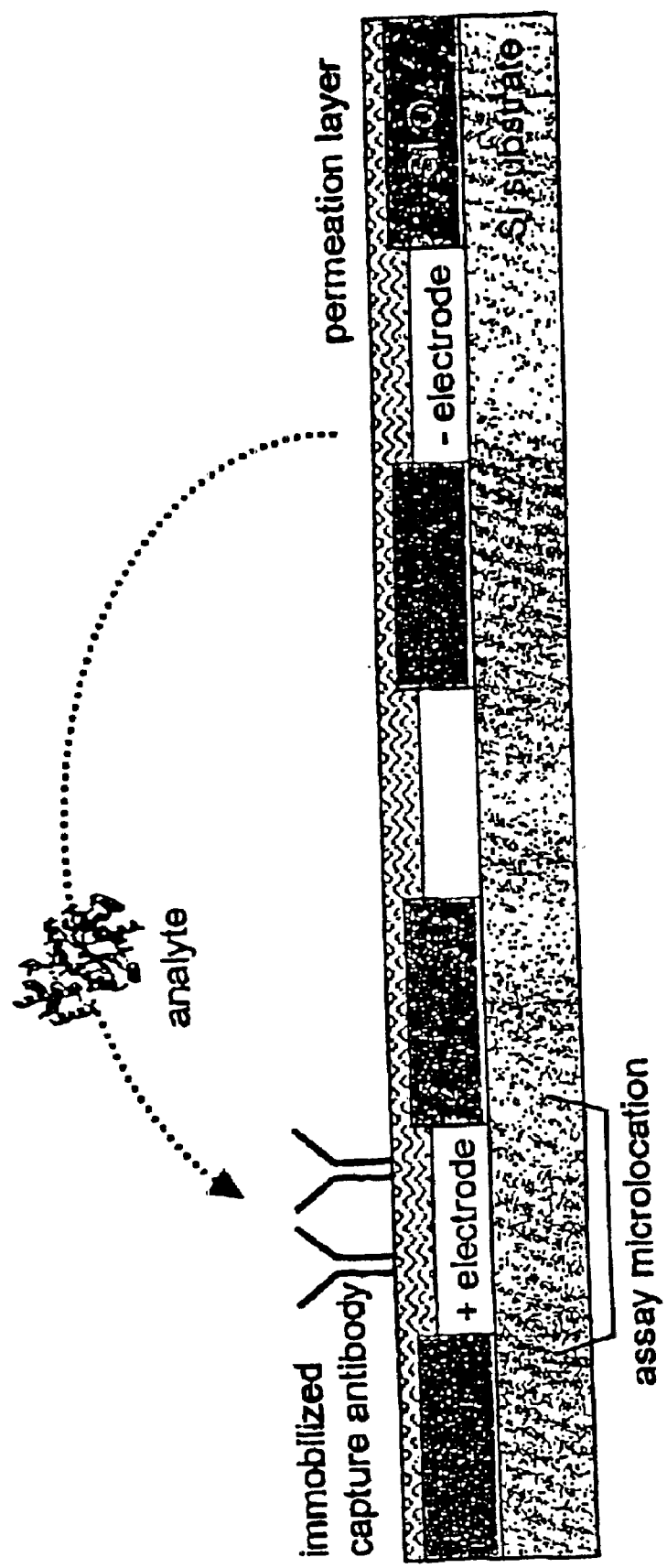
FIG. 5: An illustration of the process of electronically addressing an antigen protein to a microlocation with an immobilized capture antibody. The electrode at the desired microlocation site is biased positively to attract the protein analyte, and one or more counter electrodes (e.g., in the ring of electrodes shown in FIG. 4) or one or more non-desired microlocation electrodes, are biased negatively to generate the electric field. The proteins are specifically bound by their capture antibodies at the assay microlocations. These bound antigens may then be detected directly (if labeled prior to addressing) or by detection labeling with another antibody (or other labeling reagent) by fluorescent detection or other detection means appropriate for the labeling moiety.

As expected, fl-SEB migrates toward the positive biased electrode (anode), confirming that the protein bears a net negative charge at pH 7.5. At pH 7.5 all of the proteins being used in toxin assays should bear a negative charge and thus migrate toward a positively biased electrode and away from a negatively biased electrode, as illustrated in FIG. 5.

2B: Immobilization of Immunoreagents at the Microlocations

Monoclonal antibodies specific for SEB (Biological Defense Research Directorate, Bethesda, Md.) and CTB (Karlan Research Products Corp.) were obtained and biotinylated. The SEB-specific mouse monoclonal IgG was biotinylated to the extent of 2.5 mol biotin per mole IgG. The CTB-specific mouse monoclonal IgG (was biotinylated to an extent of 4 mol biotin per mole IgG. Biotinylation of protein lysines with biotin-XX-succinimidyl ester forms amides between the lysyl amine of the protein and the activated ester group of biotin. The reaction proceeds with the loss of a positive charge from lysine forming a neutral biotinylated derivative. The net change in charge is −1 unit for each biotin added. Both biotinylated monoclonal antibodies focused into several bands with isoelectric points ranging from 5.3 to 6.3.

Biotinylated antibodies were diluted into 50 mM histidine, pH 7.5. The Array of antibodies was electronically constructed on the chop by sequentially placing 10 $\mu$l of each antibody solution (concentration between 250 and 400 nM) on the chip, biasing up to five electrodes positively with the ring of peripheral electrodes biased negatively. Current was supplied at 400 nA per microlocation for 1 minute. A fresh solution of the antibody was then applied and the same procedure repeated. After each electrophoretic addressing step, the antibody solution was removed from the chip and the chip was washed three timed with excess phosphate buffered saline containing 0.05% Tween 20. The electronic addressing process was repeated until the entire antibody array was constructed. The antibody array was equilibrated with phosphate buffered saline for 5 minutes, and then incubated with a solution of 0.025% casein in phosphate buffered saline before further analysis.

Experiments separate from the toxin immunoassays described below showed that although the streptavidin-agarose layer over the entire surface of the chip contains streptavidin, and thus can, in principle, bind the biotinylated capture antibodies, the actual binding location of each biotinylated capture antibody was precisely determined by electronically addressing the chip. Electronic addressing was found to be a reproducible method for placing consistent amounts of capture antibodies at the microlocations (a 7.2% variation or lower). Thus, the short period of time in which the biotinylated antibody is present on the chip is not sufficient to produce a significant amount of background attachment of the antibody to the permeation layer, as opposed to the rapid attachment of the antibody at the microlocations, where it is highly concentrated.

2C: Electrophoretically Accelerated Capture of the Toxins by the Immobilized Immunoreagents The toxins, fluorescein-labeled SEB (fl-SEB) or fl-CTB, were diluted in 50 mM histidine, pH 7.5. A 10-$\mu$l sample of the analyte solution was placed on the chip and the selected microlocations were biased positively at 100 nA per location for 1 min. Generally, fl-SEB solutions were electronically addressed to locations containing biotinylated anti-SEB capture antibodies to measure specific binding of the toxin. To measure the amount of non-specific binding, the same solution was electronically addressed to microlocations that contained either biotinylated anti-CTB capture antibody or no antibody at all. The same process was repeated with fl-CTB solution. During development of the electronic methods, electronic addressing conditions were selected that gave not only the highest specific binding of the toxin to its capture antibody but also the lowest non-specific binding of the toxins to a mismatched capture antibody and a non-addressed microlocation.

Figure 6A:
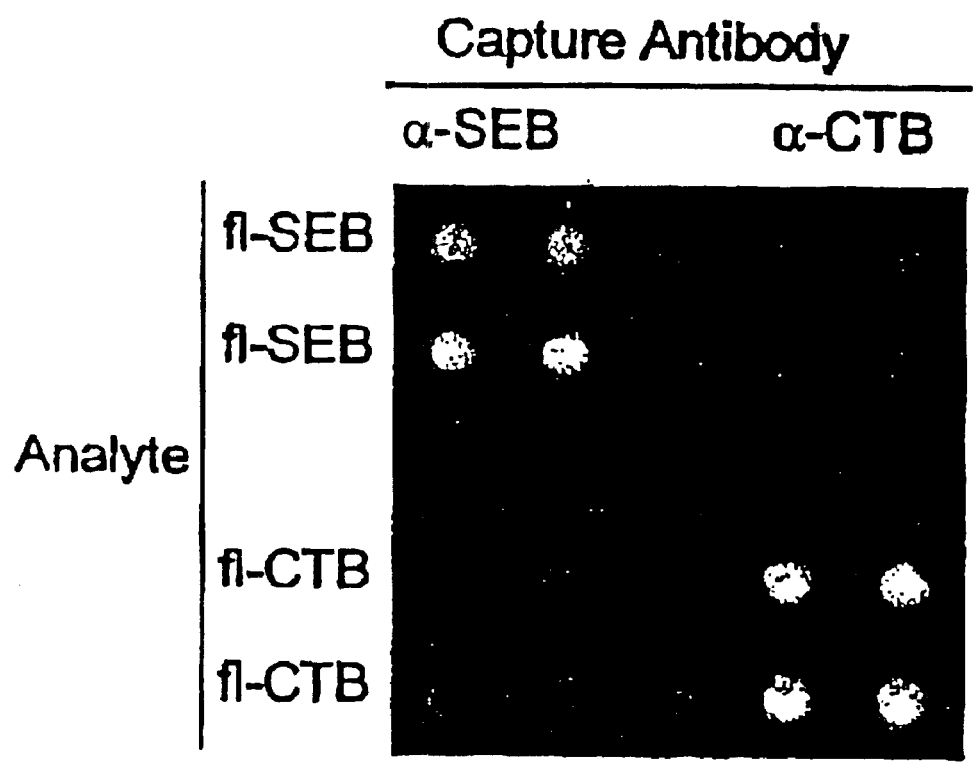
FIGS. 6A and 6B: 6A is a fluorescent image of the 5 by 5 array, after the capture electronic immunoreaction described in Example 2. Biotinylated α SEB was addressed to the two left columns of the 5 by 5 chip, and Biotinylated α SEB was addressed to the two right columns. Fluorescein labeled SEB (fl-SEB) was then addressed to the top two rows, and fluorescein labeled CTB (fl-CTB) was addressed to the bottom two rows. As shown, the antigens were specifically bound by their antibodies at the appropriate microlocations, without significant non-specific binding to the other antibody. 6B is a chart graphically depicting these results.
Figure 6B:
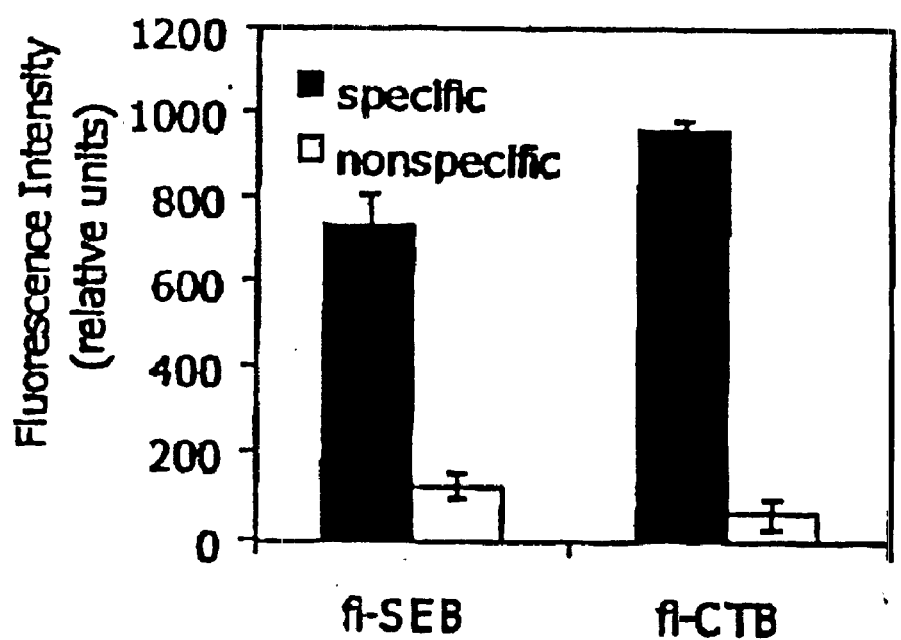
Figure 7A:
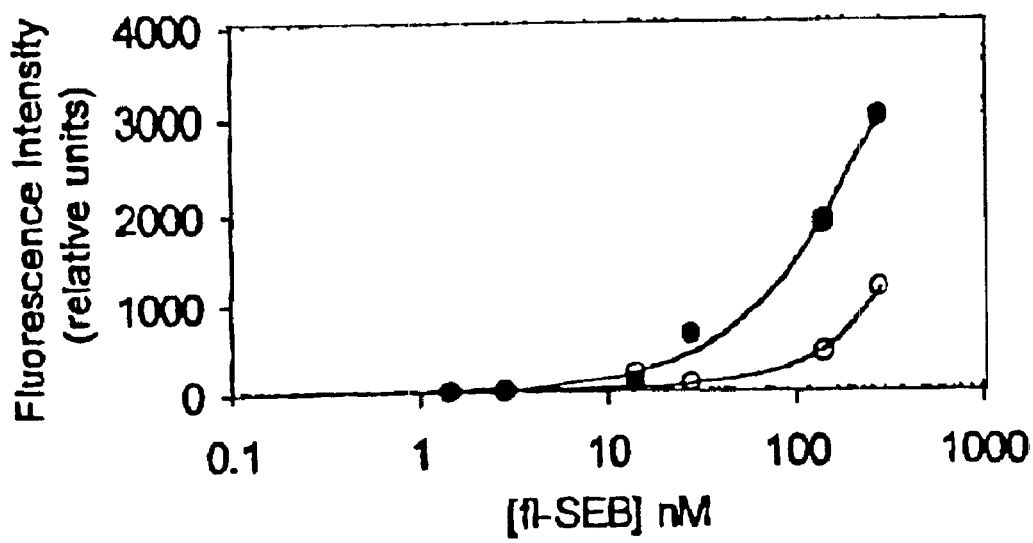
FIGS. 7A and 7B: 7A and 7B are concentration vs. increase in fluorescent intensity graphs for SEB and CTB, respectively, under both electronic addressing immunoreaction conditions and passive immunoreaction conditions. Briefly, arrays of SEB and CTB specific antibodies were prepared as described in Example 2. Solutions of fl-SEB or fl-CTB at the indicated concentrations were applied to the chip for a total of 1.5 minutes to allow for passive binding (open circles) of the toxin to the capture antibodies. For comparison, fl-SEB and fl-CTB were electronically addressed (closed circles) to specific microlocations to one minute. As can be seen from the graphs, electronic addressing dramatically increased specific binding of the toxins to the antibodies in the 10 to 100 nM range.
Figure 7B:
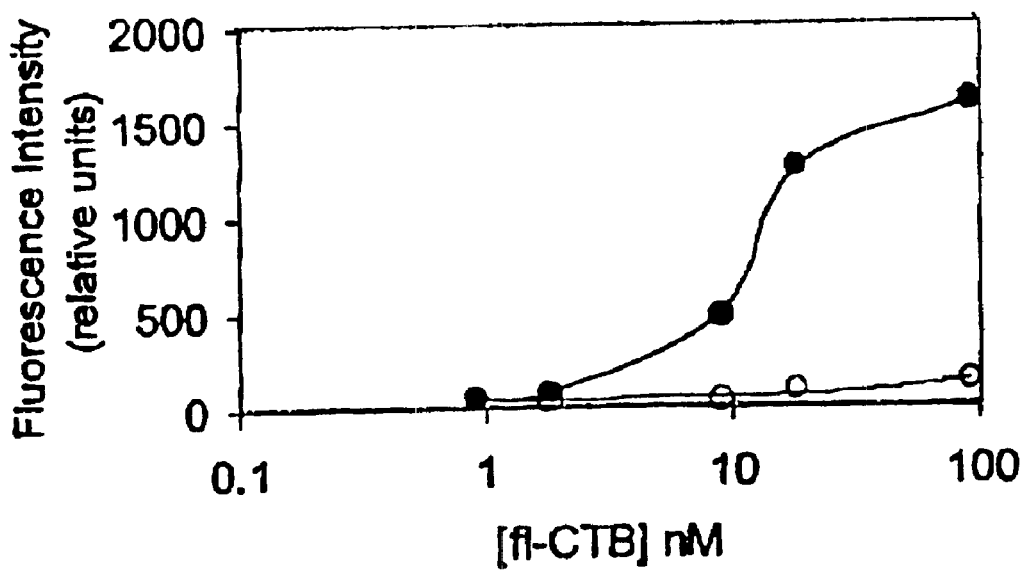

Since fl-SEB is negatively charged in a solution at pH 7.5, we positively biased the assay microlocations to attract the analyte. At a current of 100 nA per microlocation, fl-SEB rapidly accumulated over all biased microlocations. Microlocations containing SEB-capture antibodies, CTB-capture antibodies, or no capture antibody were all biased to examine the specificity of fl-SEB binding. After 1 min., the electrophoresis was stopped and the solution was washed from the chip. The results are shown in FIG. 6A. The concentrated fl-SEB bound only to the locations with SEB-capture antibody. There was little non-specific binding of fl-SEB to the mismatched CTB-capture antibody. Similarly, fl-CTB was transported to and concentrated at a positively biased microlocation from a dilute solution. Fl-CTB bound to only the locations with the CTB-specific antibody, as shown in FIG. 6A. There was little non-specific binding of CTB to the mismatched SEB-specific antibody. The same electronic method was successfully applied to both fl-SEB and fl-CTB and permitted the direct detection of both toxins within minutes after applying a solution. FIG. 6B is a chart showing a more quantitative comparison of the fluorescence data.

We noticed that no passive binding of fl-SEB or fl-CTB to their capture antibodies occurred during the brief time that the analyte solutions were in contact with the chip. Since many binding reactions are dependent on the concentration of the binding species and the length of time allowed for the binding reaction, we attributed the rapid detection achieved by the electronic addressing to the fact that this method concentrates the analyte over the assay site. In this manner the electronic addressing method facilitates binding of analyte from a dilute solution. This feature of the electronic chip over passive binding methods offers the advantage of accelerating the binding reaction.

2D: Electrophoretically Accelerated Capture of Two Toxins in a Mixture

Figure 8A:
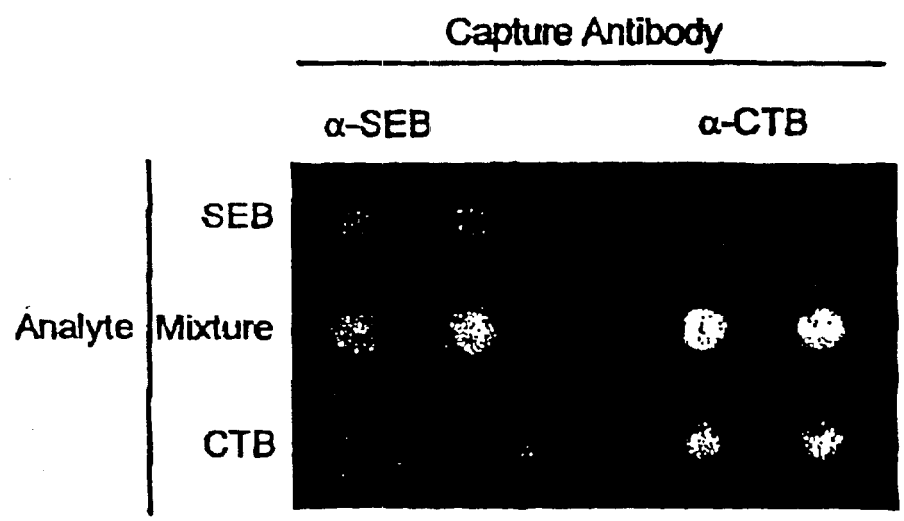
FIGS. 8A and 8B: 8A is a fluorescent image of the 5 by 5 array, after the toxin mixture capture electronic immunoreaction described in Example 2. Biotinylated α SEB was addressed to the two left columns of the 5 by 5 chip, and Biotinylated α SEB was addressed to the two right columns. A mixture of fl-SEB and fl-CTB was addressed to center row. For comparison, fl-SEB was addressed to the top row, and fl-CTB was addressed to the bottom row. As shown, the antigens were specifically bound by their antibodies at the appropriate microlocations, without significant non-specific binding to the other antibody, both in a mixture and individually. 8B is a chart graphically depicting these results.
Figure 8B:
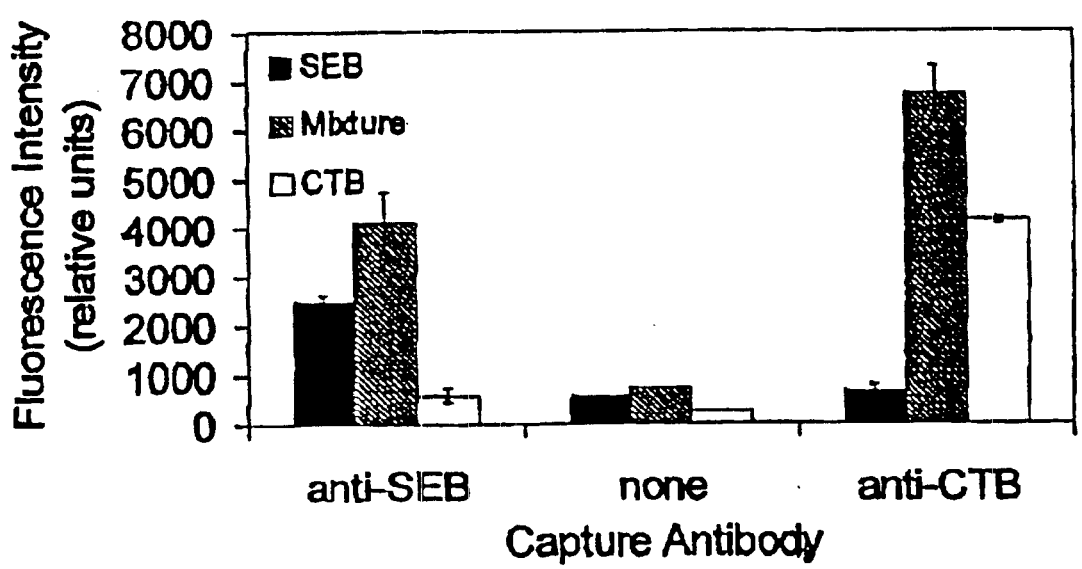

A primary interest of assay development focuses on developing platforms that allow simultaneous detection of multiple analytes. The chip integrates multiple assay locations in an array format for the simultaneous detection of multiple analytes. We investigated the possibility of detecting both fl-SEB and fl-CTB from a mixture in a single electronic addressing step. An array of SEB- and CTB-capture antibodies was addressed to the chip in the format shown in FIG. 6. A mixture of fl-SEB and fl-CTB, both at 20 nM, was electronically addressed simultaneously to microlocations that contained an SEB-capture antibody, no capture antibody, or CTB-capture antibody. Subsequently, a 20 nM solution of fl-SEB was addressed across a row of microlocations containing the same set of capture antibodies. A 20 nM solution of fl-CTB was addressed across another row of microlocations with the same set of capture antibodies. The mixture of analytes showed fluorescence bound to both the SEB- and CTB-capture antibodies. The individually addressed toxin bound only to the appropriate capture antibody, as shown in FIG. 8A. A modest binding enhancement of fl-SEB and fl-CTB to the appropriate capture antibodies was observed for the mixture of toxins (see FIG. 8B), which appears to be unique to the combination of these two toxins.

To verify that fl-SEB was bound at the site of its capture antibody and not at locations containing the CTB-specific capture antibody, the chip was incubated with a Texas Red-labeled polyclonal goat antibody specific for SEB. This antibody was diluted to 6.8 µg total IgG/ml in 0.1% BSA in phosphate-buffered saline and applied to the chip for 1 h in the dark. The chip was then washed in phosphate buffered saline containing 0.05% Tween 20. The relative amount of Texas Red fluorescence was measured and compared to the pattern of fluorescein fluorescence on the chip. This antibody bound only to the four pads that were electronically addressed with both the SEB-capture antibody and fl-SEB; there was no Texas Red binding on the pads with CTB-capture antibody. This result confirms specific binding of fl-SEB to the appropriate capture sites on an array from a simple solution and a mixture of toxins using electronic addressing.

Example 3

Immunochemical Detection of *Bacillus globigii* Spores

A single-antibody direct immunoassay was used for *B. globigii* spores, which consisted of two steps of DC current application: collecting *B. globigii* spores on the electrodes, and addressing the detecting antibodies to the electrodes. The assay was performed on 5×5 array chips. *Bacillus globigii* spores (the Biological Defense Research Directorate, Bethesda, Md.) were stocked in Phosphate Buffered Saline (PBS) (pH 7.2) (Life Technologies, Grand Island, N.Y.) at a concentration of $1.4 \times 10^9$ spores/ml. in 50 mM histidine buffer. For the *B. globigii* assay, polyclonal goat anti-*B. globigii* antibody (Biological Defense Research Directorate) and polyclonal rabbit anti-Malathion antibody (Fitzgerald Industries International, Concord, Mass.) was labeled in house with Texas Red (TR)-x-succinimidyl ester (Molecular Probes, Eugene, Oreg.), and used as the detecting antibodies.

3A: Electronic Addressing of Spores to Selected Microlocations

The surface of the flow cell was blocked with 0.1% BSA in PBS/Tween 20 overnight at 4° C. prior to experiments. For the assay, $4 \times 10^7$ spores in 40 µl of 50 mM histidine having a conductivity of 266 µS/cm, were first introduced into the flow cell through the inlet by a peristaltic pump. Spores were then collected continuously by electrophoresis onto 12 positively biased electrodes at an applied DC current of 100 nA per electrode (the DC potential was 2.4 V) for total 6 minutes. In the time segment between 1.5 minutes and 3.5 minutes after the DC current was applied, the flow cell and inlet tubing were washed by a reverse flow of 50 mM histidine for 2 minutes at 45 µ/minute in the continued presence of the DC current.

Figure 10A:
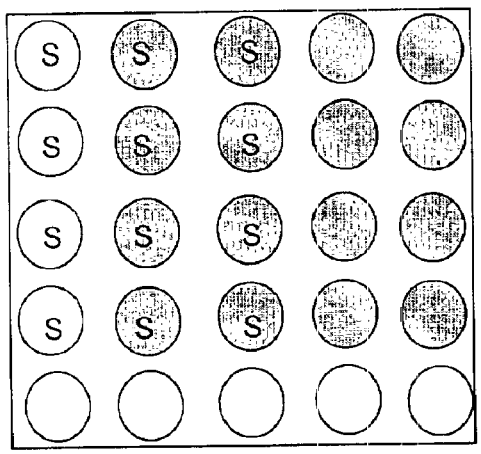
FIGS. 10A through 10E: The electric field-mediated 2-step immunoassay for *B. globigii* spores of Example 3 is depicted. 10A is a schematic representation of the addressing configuration, wherein spores were addressed to the electrodes (used as anode) marked by "S" at 100 nA per electrode for 6 min. TR-labeled polyclonal goat anti-*B. globigii* antibodies were addressed to the electrodes (used as anode) marked with "gray color" at 125 nA per electrode for 1 min. 10B is a white light image obtained after the DC electric current was applied for addressing the spores to the electrodes. 10C is a fluorescent image obtained after the DC current was applied for addressing the spores to the electrodes. 10D is a fluorescent image obtained after TR-labeled polyclonal goat anti-*B. globigii* antibodies were addressed. 10E is a chart showing the titration and specificity for *B. globigii* spore immunoassay.

Typical images for a DC field-driven spore immunoassay are shown in FIGS. 10A–E. The electrode configurations for the 5×5 chip are illustrated in FIG. 10A, in which the electrodes addressed for spores and for TR-labeled antibodies are represented by "S" and by gray-color, respectively.

Figure 10B:
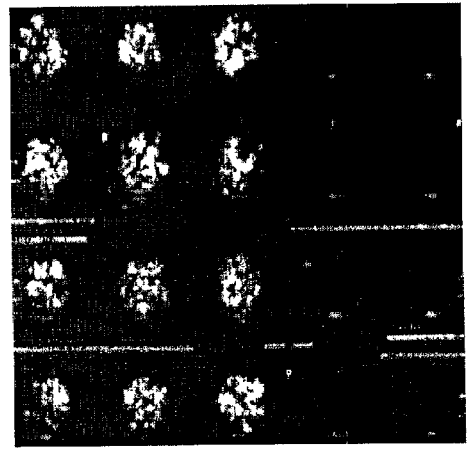
Figure 10C:

FIGS. 10B and 10C are images of the spores that were collected on 12 positively biased electrodes, due to the applied DC currents (100 nA per electrode), under white light and laser illuminations, respectively. The spores remained on the selected 12 electrodes after removal of the DC current. Their adhesion to the agarose permeation layer above the electrodes is most likely to be due to the inherent sticky nature of proteins that form the thick, outer coating of the spore. Due to their large size (~1 µm), they tend to scatter the excitation laser, which results in elevated background signals.

3B: Electronic Fluorescent α-*B.globigii* Labeling of the Spores at the Microlocations After the spore collections, TR-labeled polyclonal goat anti-*B. globigii* antibody, diluted in 50 mM histidine/0.1% Tween 20 to a final concentration of 3.1 µg/ml, was then introduced into the flow cell through the inlet at 45 µl/minute for 1 minute. The antibodies were then addressed continuously by electrophoresis to 16 positively biased electrodes at an applied DC current of 125 nA (the DC potential was 2.5 V) for 1 minute. The DC current was then turned off and the flow cell was washed by a reverse flow of histidine from the buffer reservoir for 4 minutes at 45 µl/minute to wash off any unbound antibodies. The assay process was visualized under white light and fluorescence microscopes.

Figure 10D:
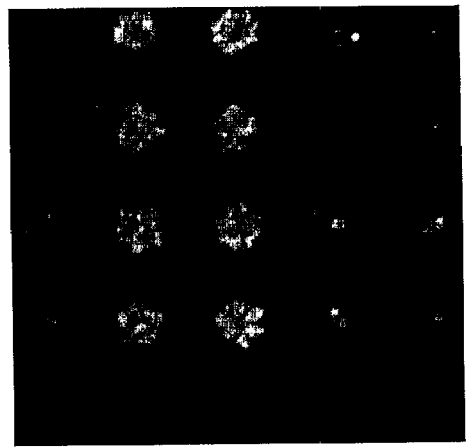

The images of the 5×5 array chip under laser illumination are shown in FIG. 10D, after 16 positively biased electrodes were addressed with TR-labeled anti-*B. globigii* spore antibodies by applying a DC current (125 nA per electrode). The effectiveness of the electronic addressing of antibodies over the passive diffusion of antibodies onto the electrodes was evident since the fluorescence levels over the electrodes addressed with both spores and antibodies were significantly greater than the electrodes addressed with only spores but not antibodies. Little non-specific binding of the detecting antibodies to the microlocations without spores occurred as indicated by the low light intensity from those microlocations. The total time for performing this assay was less than 15 minutes.

Figure 10E:
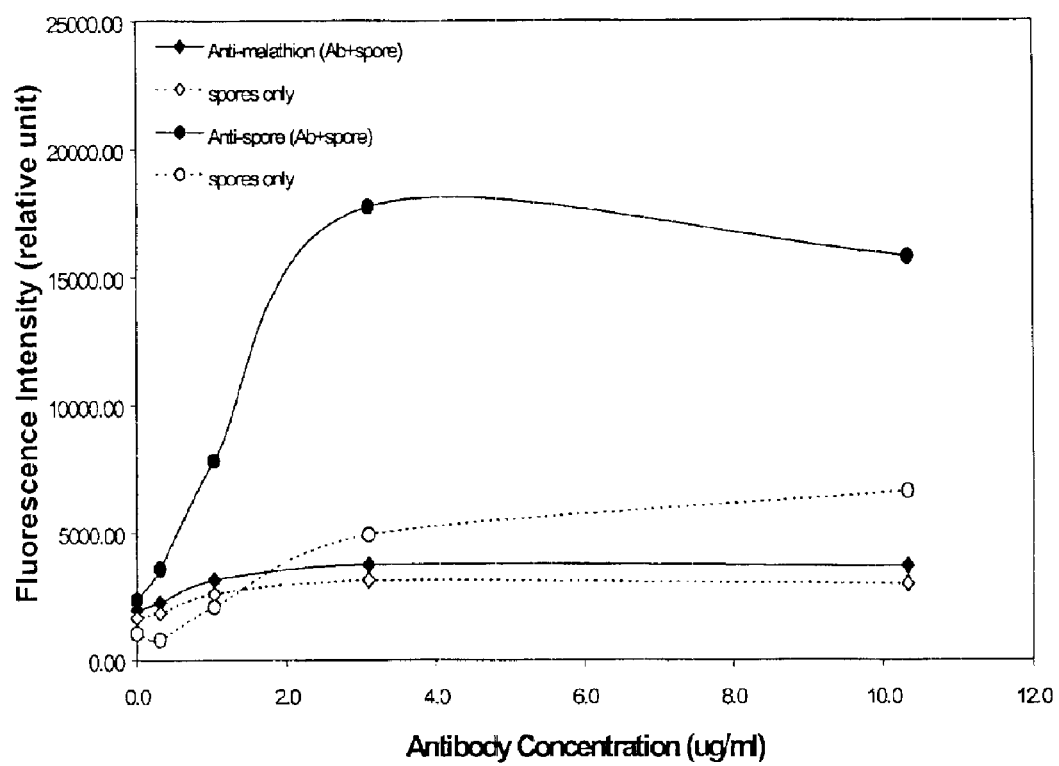

To further validate the assay, a titration curve and cross-reactivity characteristics of the detecting antibody were determined. At a given spore concentration ($10^9$/ml) and a fixed electronic condition for addressing spores onto the electrodes, a series of TR-labeled anti-*B. globigii* spore antibody concentrations (at 0.3, 1.0, 3.1, and 10.3 µg/ml) were used for electronic addressing to the spore-loaded electrodes. Comparison of fluorescent intensities between electrodes addressed with TR-labeled antibodies at different concentrations revealed that an antibody concentration of 3.1 µg/ml yielded the greatest fluorescent signals (FIG. 10E). To investigate potential cross-reactivity between spores and non-specific antibodies, a similar titration experiment was also performed for TR-labeled polyclonal rabbit anti-malathion antibodies on a separate chip. The fluorescent intensities for anti-malathion antibodies were at the fluorescence background level and were 4 to 5 times less than those for anti-spore antibodies.

To quantify the cross-reactivity of spores with non-specific antibodies (TR-anti malathion), additional experiments were performed on a single chip to ensure comparable assay conditions. After spores were electrically captured on the electrodes, the anti-spore antibodies were addressed to certain electrodes, followed by a washing process to remove any unbound antibodies. The fluorescence levels were measured on the spore-loaded electrodes with and without addressed antibody. Then the above process was repeated for the anti-malathion antibodies. The binding efficiency between spores and antibodies was quantified using the fluorescence intensity on the spore-loaded electrodes normalized against the white light intensity of the spores. This normalization took into account the variation of spore numbers on different electrodes. The ratio of the binding efficiency at the electrodes with electrically addressed antibodies to the electrodes without addressed antibodies was 13.7 for the anti-spore antibodies. This ratio was 4.2 for anti-malathion antibodies, however, indicating that there was some degree of cross-reactivity between the non-specific antibodies and the spores. The specificity of spore detection in this assay is about 3.3:1. Cross-reactivity between these spores and non-specific antibodies was also observed in ELISA assays. Compared with classical immunoassays, this DC field-mediated *B. globiggi* immunoassay has the advantages of fast reaction time (~15 minutes) and no need for additional capture antibodies.

Example 4

Dielectrophoretic Separation of *B. globigii* Spores and *E. coli*

Figure 11A:
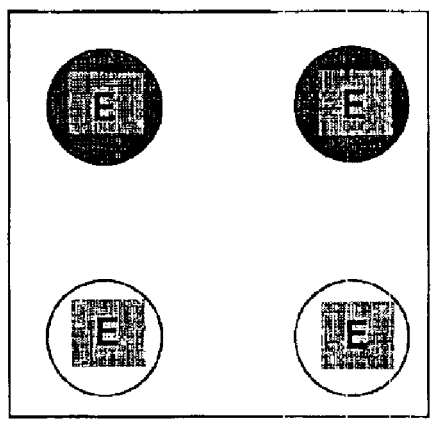
FIGS. 11A through 11E: The electric field-mediated 3-step immunoassay for *E. coli* bacteria of Example 5 is depicted. 11A is a schematic representation of the addressing configuration wherein biotinylated TR-labeled monoclonal anti-*E. coli* antibodies were addressed to the top two electrodes (used as anode, marked with "dark-gray-color") at 400 nA per electrode for 2 min. Heat-killed *E. coli* bacteria were addressed to all four electrodes (marked by letter "E") at 5 kHz, 5 V p—p for 5 min. FL-labeled goat anti-*E. coli* O157:H7 F(ab')$_2$ antibody fragments were addressed to all the four electrodes (used as anode, marked with "light-gray-color") at 200 nA per electrode for 1 min. 11B is a fluorescent image obtained after biotinylated TR-labeled monoclonal anti-*E. coli* antibodies were addressed. 11C is a white light image after heat-killed *E. coli* bacteria were addressed. 11D is a final fluorescent image after FL-labeled goat anti-*E. coli* O157:H7 F(ab')$_2$ antibody fragments were addressed. 11E is a chart of the FL-fluorescence intensity on the electrodes with and without capture antibodies.
Figure 11B:
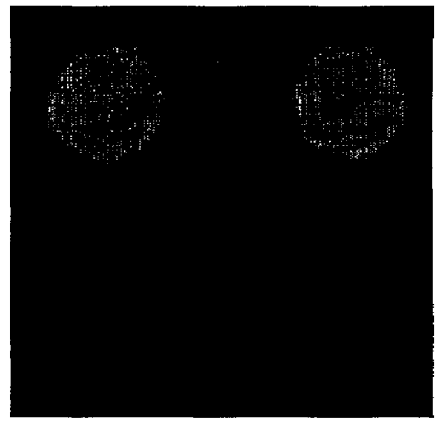
Figure 11C:
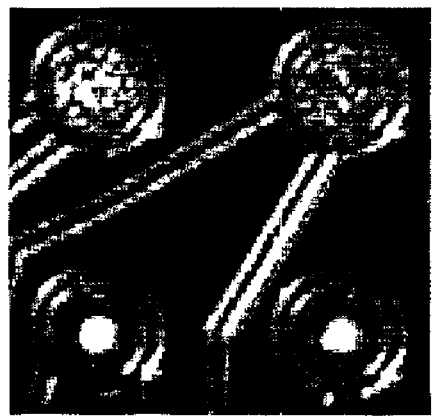

Heat-killed *E. coli* bacteria and *B. globigii* spores were washed 3 times in 280 mM mannitol (Sigma) and resuspended in the mannitol solution having a conductivity of 20 $\mu$S/cm. The final mixture concentration was $2\times10^8$/ml and $3\times10^8$/ml for bacteria spores, respectively. Microscale separation was achieved by applying an AC voltage at 50 kHz, 5 V p—p to the 5×5 array, in which adjacent electrodes along either horizontal or vertical lines were applied with signals of the opposite polarity. This method of addressing is referred to as "checkerboard" mode.

FIG. 9A shows the distribution of *B. globigii* spores and heat-killed *E. coli* O157:H7 bacteria on a 5×5 chip after an AC voltage at 50 kHz, 5 V p—p field was applied for 2 minutes. The higher magnification view in FIG. 9B reveals that the spores were collected over the electrodes under positive (high field) DEP forces whereas the bacteria were repelled from those electrodes by negative (low field) DEP forces. The differential DEP responses between the spores and *E. coli* arise from the structural and compositional differences between these particles. At 50 kHz, the poorly-conducting plasma membrane of the bacteria dominated their dielectrophoretic behavior, and the bacteria were less polarizable than the surrounding medium (conductivity 20 $\mu$S/cm) and exhibited negative DEP. Even though the spores (~1 $\mu$m in diameter) are also comprised of a poorly-conducting plasma membrane, their relatively conductive cortex and coat layers dominated the polarization characteristics of the as compared to the surrounding medium, and thus they exhibited positive DEP. This result demonstrates that two types of particles having different structural and compositional differences can exhibit different DEP characteristics and can thereby be selectively manipulated. It is worthwhile to note that the heat-killed *E. coli* bacteria exhibited little or no DEP effects when they were suspended in solutions of moderate or high conductivities (>50 $\mu$S/cm). Thus, in order to achieve appreciable DEP effects for the heat-killed *E. coli* the suspension conductivity was chosen to be a very low value of 20 $\mu$S/cm.

Example 5

Sandwich Immunoassay Detection of *E. coli*, and Verification with Model Protein Contamination System A sandwich-format immunoassay was used for detecting *E. coli* bacteria. This assay format included 3 steps: 1) immobilizing capture antibodies on electrodes with a DC current; 2) collecting *E. coli* to these electrodes in a DEP step with an AC voltage; and 3) addressing FL-labeled detecting antibodies with a DC current. The assay was performed on 5×5 array chips in 50 mM histidine buffer. As noted above, these chips were not equipped with a flow cell: rather, solutions were pipetted onto the chip.

For the *E. coli* assay, monoclonal anti-*E. coli* antibody (ViroStat, Portland, Me.), monoclonal anti-cholera toxin B (CTB) antibody (Karlan Research Products Corp., Santa Rosa, Calif.), and monoclonal anti-staphylococcal enterotoxin B (SEB) antibody (the Biological Defense Research Directorate, Bethesda, Md.) were labeled with biotinyl-xx-succinimidyl ester and TR-x-succinimidyl ester to serve as capture antibodies. Fluorescein (FL)-labeled goat anti-*E. coli* O157:H7 $F(ab')_2$ antibody fragments (KPL, Gaithersburg, Md.) was used as the detecting antibody. Protein toxin, SEB (Sigma), labeled in house with fluorescein (Sigma) (FL-SEB), and fluorescein-labeled CTB (FL-CTB) (Sigma) were used as "contamination" spikes in the *E. coli* assay. All the listed antibodies were dialyzed against 50 mM histidine buffer (conductivity of 62 $\mu$S/cm) before use.

5A: Electronic Addressing of Immunoreagents to Microlocations

A 10 $\mu$l aliquot of biotinylated TR-labeled monoclonal anti-*E. coli* capture antibody (5 $\mu$g/ml) was first micropipetted onto the chip. The antibodies were then addressed by electrophoresis to the selected, positively biased electrodes at an applied DC current of 400 nA per electrode for 2 minutes with a 10 second no current pause in the middle. The chip was then washed by pipetting with excess 50 mM histidine to remove unbound capture antibodies.

5B: Electronic Addressing of *E. coli* bacteria by DEP

A 10 $\mu$l volume of heat-killed *E. coli* bacteria ($10^8$/ml) or 10 $\mu$l of mixture of *E. coli* ($10^8$/ml) with FL-SEB (240 $\mu$g/ml) and FL-CTB (240 $\mu$g/ml) was added by pipetting onto the chip that was loaded with capture antibodies on selected electrodes. *E. coli* bacteria were then collected on the selected electrodes by applying an AC voltage of 5 kHz, 5 V p—p for 5 minutes to the electrodes. The chip was then washed extensively with 50 mM histidine buffer by pipette.

5C: Electronic Fluorescent α-*E. coli* Labeling of *E. coli* at the Microlocations To detect the presence of *E. coli* bacteria, 10 $\mu$l of FL-labeled polyclonal goat anti-*E. coli* detecting antibody (10 $\mu$g/ml) was micropipetted onto the chip and consequently addressed onto the corresponding electrodes (used as anode) at a DC current of 200 nA per electrode for 1 minute. The chip was extensively washed again with 50 mM histidine buffer to remove unbound detecting antibodies. Images were taken under white light and fluorescence microscopes.

The DC and AC field mediated sandwich assay for *E. coli* is shown in FIGS. 11 A–E. The electrode configurations for the 5×5 chip are shown in FIG. 11A, in which "E" represents the electrodes addressed with *E. coli*, "dark gray-color" represents the electrodes addressed with biotinylated TR-labeled anti-*E. coli* capture antibodies, and "lightgray-color" represents the electrodes addressed with FL-labeled detecting antibodies. Biotinylated anti-*E. coli* capture antibodies were first loaded on the top row of microlocations by applying DC current and were immobilized above the electrodes through biotin binding to streptavidin in the permeation layer (FIG. 11B). *E. coli* bacteria were then addressed to the four microlocations through DEP using AC signals at 5 kHz, 5 V p—p. It was observed that *E. coli* collection patterns were different between the microlocations with and without the capture antibodies (FIG. 11C). For the microlocations with capture antibodies (top row of microlocations), *E. coli* bacteria were dispersed over the entire microlocation area. This phenomenon was attributed to the capture of *E. coli* by specific antibodies pre-immobilized over the entire microlocations as they were attracted by DEP forces towards the field maximum, located at the center of the electrodes. In the absence of specific capture antibodies at the microlocations (bottom two microlocations), the *E. coli* bacteria were accumulated over the center regions of the electrode (FIG. 11C).

Figure 11D:
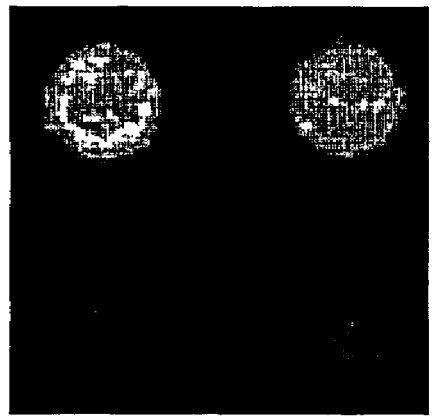
Figure 11E:
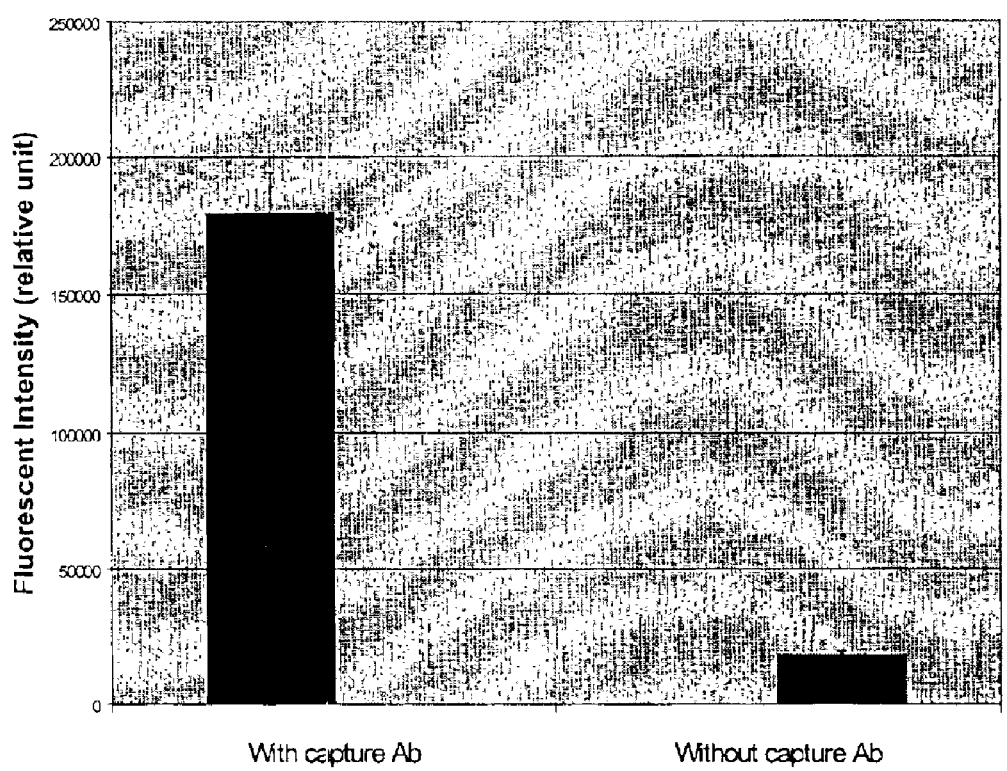

After *E. coli* bacteria were collected onto the electrodes, the AC field was turned off and a washing step was employed to remove the unbound *E. coli*. The bacteria that remained at the microlocations after washing were immunodetected by addressing the FL-labeled anti-*E. coli* detecting antibody to all of the four microlocations with a DC current (FIG. 11D). The fluorescent intensity at the microlocations with and without capture antibody was measured. According to FIG. 11E, the ratio of fluorescent intensity for microlocations with capture antibodies to that for microlocations without capture antibodies was about 9.6.

5D: Demonstration of Sandwich Assay with CTB and SEB Model Contaminants

For a sample containing multiple bioparticle types, separating one target type from the sample for the follow-up bioassay may provide advantages of reduced cross reactivity and improved signal-to-noise ratio. For example, in the application of analyzing an environmental sample that may contain micron-sized bacteria and protein toxins, it may be necessary to first separate the bacteria and protein toxins and then perform assays on purified samples. Such a separation can be achieved by selective DEP collection of bacteria from the mixture sample with an AC field. DEP forces acting on micron-sized bacteria can be $10^6$ times stronger than the forces on protein toxins (assuming a 10 nm dimension). Thus, an appropriately applied AC field configuration can result in the collection of bacteria with no effect on protein toxins. Above, the feasibility of immunoassay detection of a pure *E. coli* sample by a combined DC and AC field was shown. Below, the experiments also have shown that the method can be applied to an *E. coli* sample spiked with two fluorescein-labeled protein toxins, FL-SEB and FL-CTB, a model system for a complex biological sample mixture.

Using the above protocol, an electric field-mediated immunoassay for *E. coli* in a mixture containing FL-SEB and FL-CTB proteins was performed. After loading biotinylated TR-labeled monoclonal anti-*E. coli* capture antibodies onto the microlocations by applying a DC current, an aliquot of the mixture of *E. coli* and FL-SEB and FL-CTB was pipetted onto the chip and an AC voltage was then applied to selected electrodes. It was observed that *E. coli* bacteria were collected at the microlocations over the selected electrodes. Furthermore, the fluorescent intensity on all the microlocations, AC addressed or not, was similar, indicating that FL labeled SEB and CTB proteins were not collected by the AC field. This is different from Example 2, in which both FL-SEB and FL-CTB proteins were transported to and collected over the electrodes under the influence of a DC current. Finally, the uncollected FL-SEB and FL-CTB proteins and unbound *E. coli* were washed away with 50 mM histidine buffer, and the collected *E. coli* bacteria were detected by addressing FL-labeled polyclonal goat anti-*E. coli* detecting antibodies via a DC field. In this assay for detecting *E. coli* from a mixture, the ratio of fluorescent intensity for microlocations with capture antibodies to microlocations without capture antibodies was about 6.2, which is a similar value achieved for detecting the pure *E. coli* sample described above.

We claim:

1. A method for isolating and immobilizing at least one bioparticle of interest on an active electronic matrix chip device, wherein the device comprises: a substrate, individually addressable electrodes on the substrate, and a permeation layer overlying a plurality of the electrodes on the substrate, further wherein portions of the permeation layer over the electrodes form microlocations of the active electronic matrix chip device, further wherein at least one capture immunoreagent specific for the bioparticle of interest is attached to the permeation layer of the device at or between a plurality of microlocations, the method comprising:
    a) introducing onto the active electronic matrix device a sample solution containing the bioparticle of interest, wherein the sample solution is of a conductivity suitable for dielectrophoretic isolation of the bioparticle of interest;
    b) passing an alternating current through selected electrodes on the active electronic matrix chip device, wherein the electrodes are selected to produce areas of relatively high alternating current field strength and relatively low alternating current field strength at positions on the active electronic matrix chip device, wherein the alternating current is supplied at a suitable voltage and frequency for dielectrophoretic isolation of the bioparticle of interest, and further wherein the at least one capture immunoreagent specific for the bioparticle of interest are located at one or more positions of alternating current field strength at which the bioparticle of interest is predicted to aggregate; and
    c) maintaining the alternating current in (b) for a sufficient length of time to allow the at least one capture immunoreagent to bind to the bioparticle of interest, thereby immobilizing the bioparticle.

2. The method of claim 1 further comprising washing the permeation layer surface of the active electronic matrix chip device to remove undesired components of the sample solution mixture after step (c).

3. The method of claim 1 wherein the bioparticle of interest is detectably labeled.

4. The method of claim 3 wherein the bioparticle of interest is detectably labeled in an additional passive immunolabeling step comprising introducing onto the active electronic matrix chip device a solution comprising a detection immunoreagent specific for the bioparticle of interest, and incubating the solution on the chip for a sufficient time to allow the detection immunoreagent to bind to the bioparticle of interest.

5. The method of claim 3 further comprising a detection step wherein the presence or absence of the detectably labeled bioparticle is detected at one or more positions.

6. The method of claim 1 wherein the positions at which the bioparticle of interest is predicted to aggregate are at aggregate microlocations of the active electronic matrix device, wherein the at least one capture immunoreagent is attached at the aggregate microlocations.

7. The method of claim 6 further comprising the steps of:
    d) introducing onto the active electronic matrix chip device a solution comprising a detection immunoreagent specific for the bioparticle of interest;
    e) passing a direct current through one or more aggregate microlocations, wherein the electrodes under the aggregate microlocations are biased so as to attract the detection immunoreagent to the aggregate microlocations from the solution; and f) maintaining the direct current in (e) for a sufficient time to allow the detection immunoreagent to bind to the bioparticle of interest at the aggregate microlocation.

8. The method of claim 7 further comprising a detection step wherein the presence or absence of the detection immunoreagent is detected at one or more aggregate microlocations.

9. A method for isolating and detectably labeling at least one bioparticle of interest on an active electronic matrix chip device, wherein the device comprises: a substrate, individually addressable electrodes on the substrate, and a permeation layer overlying a plurality of the electrodes on the substrate, further wherein portions of the permeation layer over the electrodes form microlocations of the active electronic matrix chip device, the method comprising:

a) introducing onto the active electronic matrix device a sample solution containing the bioparticle of interest, wherein the sample solution is of a conductivity suitable for dielectrophoretic isolation of the bioparticle of interest;

b) passing an alternating current through selected electrodes on the active electronic matrix chip device, wherein the electrodes are selected to produce areas of relatively high alternating current field strength and relatively low alternating current field strength at positions on the active electronic matrix chip device, wherein the alternating current is supplied at a suitable voltage and frequency for dielectrophoretic isolation of the bioparticle of interest, and further wherein one or more positions of alternating current field strength at which the bioparticle of interest is predicted to aggregate are at one or more aggregate microlocations of the active electronic matrix chip device;

c) maintaining the alternating current in (b) for a sufficient length of time to allow the bioparticle of interest to aggregate at the aggregate microlocations;

d) introducing onto the active electronic matrix chip device a solution comprising a detection immunoreagent specific for the bioparticle of interest;

e) passing a direct current through one or more aggregate microlocations, wherein the electrodes under the aggregate microlocations are biased so as to attract the detection immunoreagent to the aggregate microlocations from the solution; and f) maintaining the direct current in (e) for a sufficient time to allow the detection immunoreagent to bind to the bioparticle of interest at the aggregate microlocation, thereby detectably labeling the bioparticle.

10. The method of claim 9 further comprising washing the permeation layer surface of the active electronic matrix chip device to remove undesired components of the sample solution mixture after step (c).

11. The method of claim 9 further comprising a detection step wherein the presence or absence of the detection immunoreagent is detected at one or more aggregate microlocations.

12. The method of claim 11 further comprising a washing step to remove unbound detection immunoreagent from the active electronic matrix chip device prior to the detecting step.

13. The method of claim 9 wherein at least one capture immunoreagent specific for the bioparticle of interest is attached to the permeation layer of the device at the aggregate microlocations, further wherein the alternating current in step (b) is maintained for a sufficient length of time to allow the at least one capture immunoreagent to bind to the bioparticle of interest.

14. The method of claim 9 wherein the bioparticle of interest adheres to the permeation layer of the aggregate microlocations due to the inherent physical or chemical properties of the bioparticle.

* * * * *